US008840560B2

(12) United States Patent
Hossack et al.

(10) Patent No.: US 8,840,560 B2
(45) Date of Patent: Sep. 23, 2014

(54) ULTRASOUND CATHETER AND HAND-HELD DEVICE FOR MANIPULATING A TRANSDUCER ON THE CATHETER'S DISTAL END

(75) Inventors: Norman Hugh Hossack, Folsom, CA (US); Richard Scott Huennekens, San Diego, CA (US); Rovil Rae Pascual Arcia, Citrus Heights, CA (US); Ernest W. Heflin, Pleasanton, CA (US); Stephen C. Davies, Folsom, CA (US); Richard Klosinski, Carmichael, CA (US); Blair D. Walker, Mission Viejo, CA (US); Chak M. Leung, Palo Alto, CA (US)

(73) Assignee: Volcano Corporation, San Diego, CA (US)

( * ) Notice: Subject to any disclaimer, the term of this patent is extended or adjusted under 35 U.S.C. 154(b) by 883 days.

(21) Appl. No.: 11/696,573

(22) Filed: Apr. 4, 2007

(65) Prior Publication Data

US 2008/0009745 A1   Jan. 10, 2008

Related U.S. Application Data

(60) Provisional application No. 60/789,001, filed on Apr. 4, 2006.

(51) Int. Cl.
| *A61B 8/14* | (2006.01) |
| *A61B 8/00* | (2006.01) |
| *A61B 17/22* | (2006.01) |
| *A61B 8/12* | (2006.01) |
| *A61B 8/08* | (2006.01) |
| *A61B 17/00* | (2006.01) |

(52) U.S. Cl.
CPC ............... *A61B 8/4488* (2013.01); *A61B 8/445* (2013.01); *A61B 8/4483* (2013.01); *A61B 17/2202* (2013.01); *A61B 2017/003* (2013.01); *A61B 8/12* (2013.01); *A61B 8/4461* (2013.01); *A61B 8/483* (2013.01); *A61B 8/0883* (2013.01)
USPC ......................................................... 600/463

(58) Field of Classification Search
CPC ................................ A61B 8/12; A61B 8/4461
USPC ......................................................... 600/463
See application file for complete search history.

(56) References Cited

U.S. PATENT DOCUMENTS

| 3,470,876 A | 10/1969 | Barchilon |
| 3,938,502 A | 2/1976 | Bom |

(Continued)

FOREIGN PATENT DOCUMENTS

| EP | 1350471 A1 | 10/2003 |
| GB | 2287375 | 9/1995 |
| WO | WO 97/23865 | 7/1997 |

OTHER PUBLICATIONS

Hellenbrand W., Fahey, J., McGowan, F., Weltin, G., Kleinman, C., "Transesophageal Echocardiographic Guidance of Transcatheter Closure of Atrial Septal Defect", American Journal of Cardiology, 1990, pp. 207-213, vol. 66, No. 2, Elsevier, New York, U.S.A.

(Continued)

*Primary Examiner* — Tse Chen
*Assistant Examiner* — Hien Nguyen
(74) *Attorney, Agent, or Firm* — Haynes and Boone, LLP

(57) ABSTRACT

A hand-operated intracardiac echocardiography (ICE) catheter is described for flexed and rotational steering is described for improved catheter operation, control and less trauma on patients. The disclosed catheter assembly includes ultrasound transducers mounted upon a rotatable tip mounted on a distal end of a flexible elongate shaft. A set of steering lines are controlled by a steering actuator to articulate bidirectionally a distal segment of the catheter. Another steering actuator controls rotation of a torque member that, in turn is coupled to the rotatable tip. A user, through the steering actuators, affects repositioning the ultrasonic transducers by repositioning exposed control surfaces of the steering actuators lengthwise along the housing of the handle.

25 Claims, 30 Drawing Sheets

(56) References Cited

U.S. PATENT DOCUMENTS

| | | |
|---|---|---|
| 4,273,111 A | 6/1981 | Tsukaya |
| 4,461,282 A | 7/1984 | Ouchi et al. |
| 4,462,408 A | 7/1984 | Silverstein et al. |
| 4,586,923 A | 5/1986 | Gould et al. |
| 4,605,009 A | 8/1986 | Pourcelot et al. |
| 4,809,704 A | 3/1989 | Sogawa et al. |
| 4,826,087 A | 5/1989 | Chinery |
| 4,841,977 A | 6/1989 | Griffith et al. |
| 4,917,097 A | 4/1990 | Proudian et al. |
| 4,996,974 A | 3/1991 | Ciarlei |
| 5,190,050 A | 3/1993 | Nitzsche |
| 5,199,950 A | 4/1993 | Schmitt et al. |
| 5,203,338 A * | 4/1993 | Jang ................ 600/463 |
| 5,207,225 A | 5/1993 | Oaks et al. |
| 5,291,893 A | 3/1994 | Slayton |
| 5,345,940 A | 9/1994 | Seward et al. |
| 5,368,037 A | 11/1994 | Eberle et al. |
| 5,385,148 A | 1/1995 | Lesh et al. |
| 5,402,793 A | 4/1995 | Gruner et al. |
| 5,413,107 A | 5/1995 | Oakley et al. |
| 5,462,527 A * | 10/1995 | Stevens-Wright et al. ... 604/528 |
| 5,527,279 A | 6/1996 | Imran |
| 5,662,606 A | 9/1997 | Cimino et al. |
| 5,713,363 A | 2/1998 | Seward et al. |
| 5,803,083 A | 9/1998 | Buck et al. |
| 5,846,205 A | 12/1998 | Curley et al. |
| 5,853,368 A | 12/1998 | Solomon et al. |
| 5,857,974 A | 1/1999 | Eberle et al. |
| 5,876,345 A | 3/1999 | Eaton et al. |
| 5,938,616 A | 8/1999 | Eaton et al. |
| 5,954,654 A * | 9/1999 | Eaton et al. ................ 600/462 |
| 6,030,360 A | 2/2000 | Biggs |
| 6,129,672 A | 10/2000 | Seward et al. |
| 6,149,599 A | 11/2000 | Schlesinger et al. |
| 2003/0149422 A1 * | 8/2003 | Muller ..................... 604/528 |
| 2004/0106897 A1 * | 6/2004 | Thompson et al. ....... 604/95.04 |
| 2004/0176691 A1 | 9/2004 | Edwardsen et al. |
| 2004/0181140 A1 * | 9/2004 | Falwell et al. .............. 600/374 |
| 2005/0222554 A1 * | 10/2005 | Wallace et al. ............... 606/1 |
| 2005/0228290 A1 * | 10/2005 | Borovsky et al. .......... 600/466 |

OTHER PUBLICATIONS

Ren J., Schwartzman, D., Michele, J., Li, K., Hoffmann, J., Brode, S., Lighty, G., Dillon, S., Chaudhry, F., "Lower Frequency (5 MHZ) Intracardiac Echocardiography in a Large Swine Model: Imaging Views and Research Applications", Ultrasound in Medicine and Biology, 1997, pp. 871-877, vol. 23, No. 6, Elsevier, New York, U.S.A.

Schwartz, S., Pandian, N., Kusay, B., Kumar, R., Weintraub, A., Katz, S., Aronovitz, M., "Real-Time Intracardiac Two-Dimensional Echocardiography: An Experimental Study of In Vivo Feasibility, Imaging Planes, and Echocardiographic Anatomy", Echcardiography, 1990, pp. 443-455, vol. 7, No. 4, Futura Publishing Company, Mount Kisco, U.S.A.

Valdes-Cruz, L., Sideris, E., Sahn, D., Murillo-Olivas, A., Knudson, O., Omoto, R., Kyo, S., Gulde, R., "Transvascular Intracardiac Applications of a Miniaturized Phased-Array Ultrasonic Endoscope. Initial Experience with Iintracardiac Imaging in Piglets", Circulation, 1991, pp. 1023-1027, vol. 83, No. 3, American Heart Association, Dallas, U.S.A.

International Search Report dated Jan. 28, 2008, for PCT/US07/65970.

Written Opinion dated Jan. 28, 2008, for PCT/US07/65970.

European Search Report and opinion for EP Application No. 07797199.2, mailed Dec. 6, 2010, 7 pages.

* cited by examiner

ULTRASOUND CATHETER AND HAND-HELD DEVICE FOR MANIPULATING A TRANSDUCER ON THE CATHETER'S DISTAL END

CROSS-REFERENCE TO RELATED APPLICATION

This application claims priority of U.S. provisional application Ser. No. 60/789,001 filed on Apr. 4, 2006, entitled "ULTRASOUND CATHETER AND HAND-HELD DEVICE FOR MANIPULATING A TRANSDUCER ON THE CATHETER'S DISTAL END," the contents of which are expressly incorporated herein by reference in their entirety including the contents and teachings of any references contained therein.

FIELD OF THE INVENTION

The present invention generally relates to ultrasound catheters. More specifically, the present invention pertains to an ultrasound intracardiac echocardiography (ICE) catheter with flexed steering to transmit ultrasound and receive echo in intracardiac diagnostics.

BACKGROUND OF THE INVENTION

Diagnostic and therapeutic ultrasound catheters have been designed for use inside many areas of the human body. In the cardiovascular system, two common diagnostic ultrasound methods are intravascular ultrasound (IVUS) and intracardiac echocardiography (ICE). Typically a single rotating transducer or an array of transducer elements is used to transmit ultrasound at the tips of the catheters. The same transducers (or separate transducers) are used to receive echoes from the tissue. A signal generated from the echoes is transferred to a console which allows for the processing, storing, display, or manipulation of the ultrasound-related data.

IVUS catheters are typically used in the large and small blood vessels (arteries or veins) of the body, and are almost always delivered over a guidewire having a flexible tip. ICE catheters are usually used to image the chambers of the heart and surrounding structures. Commercially-available ICE catheters are not designed to be delivered over a guidewire, but instead have distal ends which can be articulated by a steering mechanism located in a handle at the proximal end of the catheter.

One type of ICE catheter (EP Medsystems ViewFlex™ Intracardiac Ultrasound Deflectable catheter) has a distal articulation in a single plane (both directions), operated by a single wheel that rotates about the lengthwise axis of the handle. The wheel is turned to a specific position for the desired catheter shape, staying in place due to the inherent friction on the wheel mechanism. The catheter is torquable, and can be rotated with the handle to aid steering in a second plane. The motions required to simultaneously torque and rotate the catheter often require two-handed operation.

Another type of ICE catheter (Siemens/ACUSON AcuNav™ Ultrasound Catheter) has an additional steering plane, and each steering plane is utilized by turning one of two corresponding wheels on the handle. These wheels rotate about the lengthwise axis of the handle. A third wheel, which also rotates about the lengthwise axis of the handle, is a locking mechanism for freezing each of the two steering wheels in its respective orientation. The entire catheter need not be torqued. However, unlocking the locking mechanism unlocks the steering wheels for both of the steering planes/wheels at the same time. While the physician is steering the catheter in one plane, the orientation of the other plane may spontaneously change to an undesired orientation. Though the two steering planes allow a large combination of possible catheter configurations, the simultaneous steering of both planes in order to achieve a specific configuration can be difficult to visualize and coordinate. Further the signal lines are formed on a flex cable with a rectangular cross-section and assembled without radial symmetry. The flex cable runs along the length of the AcuNav™ catheter behind the ultrasound transducers, causing the catheter to have different bending stiffness along different bending planes of the catheter, making the catheter more difficult to manipulate or maneuver.

Both the ViewFlex and the AcuNav catheters utilize a linear array of multiple transducer elements, e.g., 64 elements, at their tips. The design of the catheter requires 64 channels in the ultrasound console in order to process each element in parallel. This requires that the catheter shaft contain at least that many conductors to carry the signals to the proximal end. There is a limit (due to conductor size, dielectric properties, etc.) to how small the catheter shaft can be made using this design. For example, the AcuNav is currently an 8 F catheter and the ViewFlex is a 9 F catheter. In order to place these catheters within the vascular system of the patient, punctures of a diameter larger than the catheter shaft size are required. These are relatively large punctures, especially when inserted arterially, and may take longer to close or heal as well as have a greater number of related complications. In addition, because many of the cases performed in the cardiac catheter laboratory or electrophysiology laboratory require multiple catheters, having a large diameter ICE catheter can cause a "traffic jam" inside the anatomy.

SUMMARY OF THE INVENTION

A hand-operated catheter assembly is useful in a variety of applications including ICE procedures for imaging intracardiac and surrounding structures with a heightened level of control and ease of use. More particularly a hand-operated ultrasound catheter assembly is described herein that includes an elongate flexible shaft having a proximal end and a distal end. An ultrasonic transducer is mounted proximate the distal end to facilitate acquiring raw ultrasound image data. In accordance with exemplary embodiments described herein the catheter assembly also includes a handle coupled to the shaft near the proximal end.

The handle includes a number of features for improved, single-handed control of the position of the ultrasonic transducer. A housing of the handle has an elongate shape adapted for hand-held operation. The handle also includes a first steering actuator for controlling a position of the ultrasonic transducer. In accordance with illustrative embodiments, the first steering actuator affects repositioning the ultrasonic transducer by repositioning an exposed control surface of the first steering actuator lengthwise along the housing of the handle. In accordance with illustrative embodiments the handle also includes a second steering actuator for controlling the position of the ultrasonic transducer. The second steering actuator affects repositioning the ultrasonic transducer by repositioning an exposed second control surface of the second steering actuator lengthwise along the housing.

The steering actuators are used to position the ultrasonic transducer in potentially a variety of ways. A first way involves rotating a tip at the end of the catheter to face the transducer in a particular direction. A second way involves flexing a distal segment of the catheter shaft upon which the transducer is mounted. A locking mechanism is also provided in accordance with particular exemplary embodiments to hold the actuators in a desired position.

BRIEF DESCRIPTION OF THE DRAWINGS

The various features of the present invention and the manner of attaining them will be described in greater detail with reference to the following description, claims, and drawings, wherein reference numerals appear in more than one drawing, where appropriate, to indicate a correspondence between the referenced items, and wherein:

It should be understood that the sizes of the different components in the figures may not be in proportion and are shown for visual clarity and for the purpose of explanation.

DETAILED DESCRIPTION OF THE DRAWINGS

The following embodiments are related to an ultrasound catheter assembly 10. For the purpose of illustration the ultrasound catheter assembly 10 is described in the context of an ultrasound catheter system for use as an intracardiac echocardiography (ICE) catheter. However, other applications of the disclosed catheter assembly are contemplated for alternative embodiments.

Figure 1:
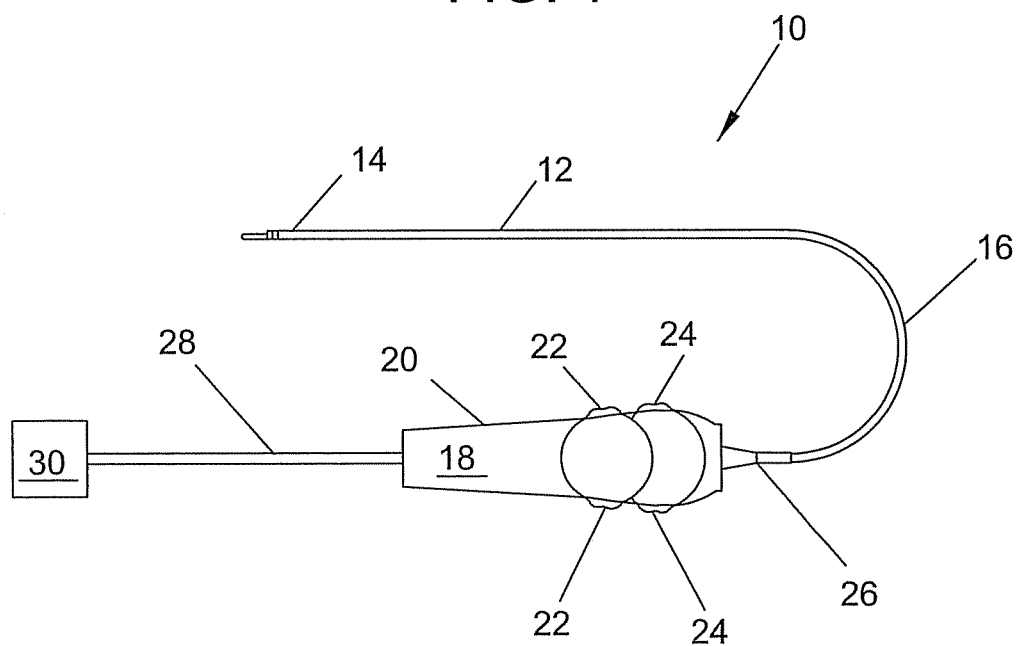
FIG. 1 is an illustration of an intracardiac echocardiography (ICE) catheter.

FIG. 1 illustratively depicts an embodiment of the catheter assembly 10 including a catheter shaft 12. The catheter shaft 12 is a generally flexible elongate member having a distal segment 14, a proximal segment 16, and at least one lumen (not shown). The proximal segment 16 is attached to a handle 18. The handle 18 includes, by way of example, a housing 20, a first in-line steering actuator 22 (e.g., a knob), and a second steering actuator 24.

The first and second actuators 22 and 24 are manipulated by a user moving an exposed control surface of the actuators 22 and 24 (using a finger/thumb) lengthwise along the length of the housing 20 of the handle 18 (as opposed to across the width of the handle 18). As used herein the term "lengthwise along the housing" includes the arrangement depicted in the exemplary embodiments (e.g., FIGS. 18, 19 and 25) as well as other arrangements where the movement of an exposed control surface of the actuators is primarily along the lengthwise axis of the handle 18 (e.g., tilted by 30 degrees). "Exposed control surface" refers to a portion of the actuators 22 and 24 that is physically accessible to a user's finger/thumb through, for example, an opening in the housing 20. Furthermore, a variety of actuator mechanisms are envisioned for actuators 22 and 24 in alternative embodiments. In the illustrative embodiment, the first actuator 22 and second actuator 24 comprise rotatable knobs that rotate on an axis that is transverse to the lengthwise axis of the handle 18 when a user moves a thumb along the handle 18's length. In alternative embodiments, thumb-controlled slider actuators replace the rotating knobs.

The distal segment 14 is, by way of example, 10 cm long. However, an exemplary range for the length of the distal segment 14 is from 5 cm to 20 cm. A tip of the distal segment 14 has a generally smaller diameter than the diameter of the proximal segment 16 of the catheter shaft. The catheter shaft 12 is made, by way of example, of engineered nylon (such as Pebax® polyether block amide) and includes a tube or tubing, alternatively called a catheter tube or catheter tubing that has at least one lumen.

In the illustrative example in FIG. 1, the first and second steering actuators 22 and 24 are accessible (have exposed control surfaces through the housing 20) on two sides of the handle 18. A potential advantage of the depicted arrangement of the steering actuators 22 and 24 is the ability of a user to control the actuators 22 and 24 with a same hand that is holding the handle 18. A strain relief 26 protects the catheter shaft 12 at a point where the catheter shaft proximal segment 16 meets the handle 18. A cable 28 connects the handle 18 to a connector 30. The connector 30, which can be any of many possible configurations, is configured to interconnect with an ultrasound system for processing, storing, manipulating, and displaying data obtained from signals generated by a sensor mounted at the distal segment 14 of the catheter shaft 12.

Figure 2:
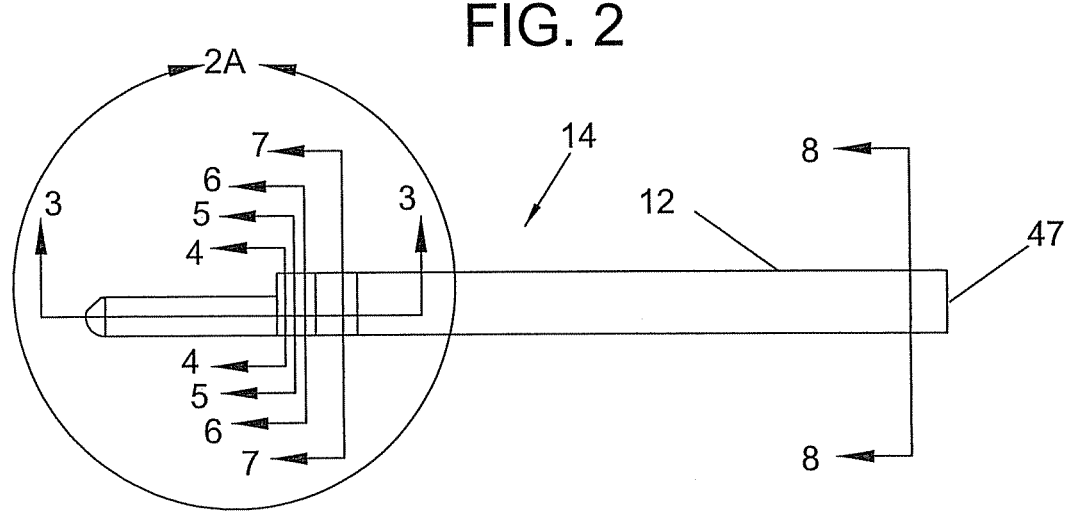
FIG. 2 is an illustration of the distal end of the ICE catheter.
Figure 2A:
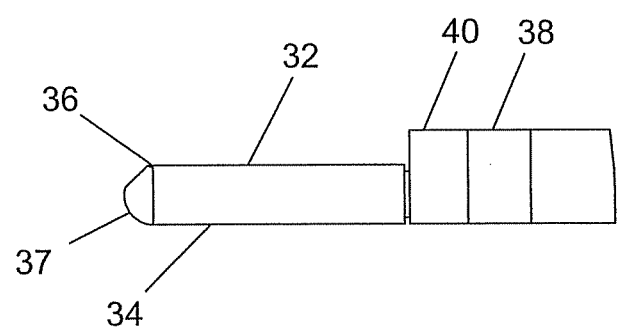
FIG. 2A is a detail view of the distal end of the ICE catheter.

FIGS. 2, 2A, 2B, and 8 illustrate a first embodiment of an ultrasound catheter 10 incorporating a handle and knob-based actuator control mechanism that supports single-handed position manipulation/control by a user of a sensor mounted at the distal segment 14 of the catheter shaft 12. Turning to FIGS. 2 and 2A, the distal segment 14 of the catheter shaft 12 includes a rotatable tip 34 that extends from the distal segment 14 and rotates relative to an axis of the catheter shaft 12. The catheter shaft 12 has a lumen 47 as illustrated more clearly in FIGS. 7 and 8.

In the illustrative embodiment depicted in FIGS. 2 and 2A the rotatable tip 34 comprises a transducer probe assembly including transducers and a flex circuit. By way of example, the rotatable tip 34 comprises a linearly arranged transducer array 32 including a set of transducer elements that are rectangular in shape, and the transducer probe assembly generally has a diameter that is smaller than the diameter of the distal segment 14 of the catheter shaft 12. Furthermore rotatable tip 34 connects to a distal segment of the catheter 10 with a rotatably smooth sliding contact. The rotatable tip 34 includes a backing material 36. The rotatable tip 34 also includes a rounded tip portion 37 (atraumatic) to reduce the incidence of trauma to the human body as the tip 34 is fed into a patient. The rounded tip portion 37 is made from material such as a room temperature vulcanizing (RTV) elastomer or any silicone rubber. The transducer array 32 is isolated from bodily fluids by the same materials as utilized in the rounded tip portion 37.

The rotatable tip 34 is potentially rotatable by manual or motorized means. The rotatable tip 34 can be adapted to rotate in a variety of angular rotational ranges. For example, in one embodiment the tip 34 is rotated bidirectionally in a 360° field of view. Alternatively the tip 34 rotation is restricted to rotate bidirectionally in a limited rotational range, e.g., clockwise or counter-clockwise by 180° in each direction. In a first embodiment, the rotating tip 34 is rotated by manipulation of the first in-line steering actuator 22 of the handle 18, and is capable of approximately 180° of rotation in the clockwise direction and 180° rotation in the counter-clockwise direction.

Figure 2B:
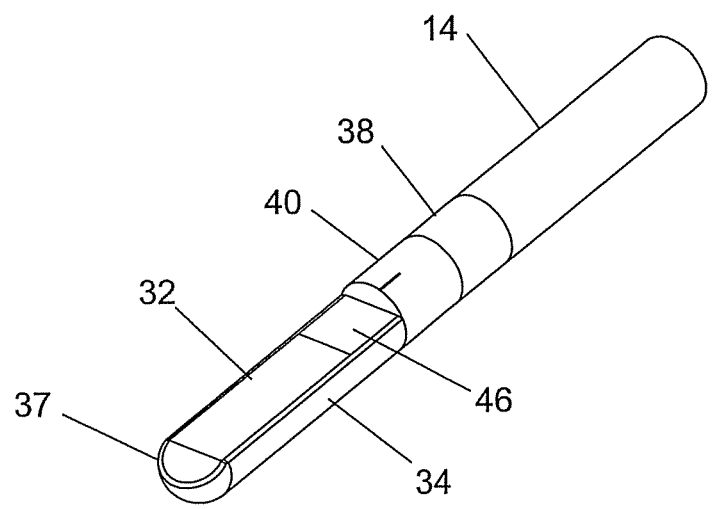
FIGS. 2B and 2C are illustrations of rotational steering mode of an ICE catheter.
Figure 2C:
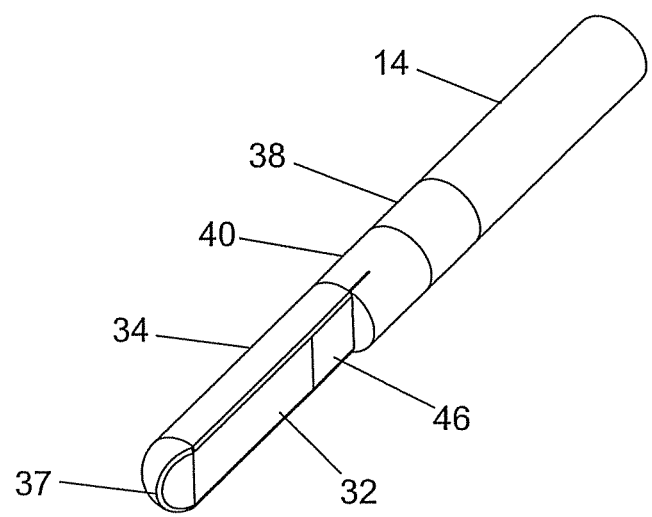

FIGS. 2B and 2C illustrate rotational steering affected by the actuator 22 of the catheter assembly 10. FIG. 2B illustrates the distal segment 14 in a central, neutral, or intermediate/relaxed position in between the two extremes of tip 34's rotation in relation to a distal segment termination 40 of the catheter shaft 12. In order to rotationally steer the transducer array 32 to the rotated position illustrated in FIG. 2C, the first steering actuator 22, a rotating knob, is turned in a first rotational direction with respect to the relatively fixed position of the handle 18. The disclosed rotational steering mechanism facilitates smooth panning movement and pinpoint accuracy in imaging the desired tissue with the transducer array 32. To rotate the catheter tip 34 in the opposite direction (e.g., counter-clockwise), the first steering actuator 22 (e.g., rotating knob) is moved in an opposing second rotational direction with respect to the handle 18.

In the illustrative embodiment depicted in FIG. 2A, the exemplary transducer array 32 is a linear array of 64 transducer elements that are individually controlled to fire and sense echoes in phases, but can alternatively be any number of transducer elements, for example 16, 32, 128 or 256. Alternatively the transducer array can be a curved array. In addition, the array can be a two-dimensional array, for example, two rows of 16 elements or four rows of 16 elements.

The transducer array illustrated in this embodiment is coupled to a single multiplexer chip 46 controlling the transmission/reception of signals to/from the array 32. In an exemplary embodiment a multiplexer effectively reduces the number of wires passing through the majority of the length of the catheter shaft 12 by one half the transducer signal wires; for example, processing the signals received on 64 transducer elements with 32 electrical conduits instead of 64. In yet other exemplary multiplexers, further reduction is achieved by a factor of four, eight, or more. Whereas commercially-available intracardiac echocardiography catheter shafts are typically 8 French to 10 French in diameter, the multiplexing in the present system provides for a catheter shaft that is 6 French or smaller in diameter. This results in a less invasive procedure and less trauma to the patient. As a result of the smaller diameter of the catheter shaft of the present system, the size of the puncture in the access artery or vein (e.g., femoral vein, femoral artery, subclavian vein, jugular vein) is smaller, allowing for faster healing, fewer complications, more space for other catheters and an ability to perform procedures in smaller patients such as pediatric patients.

Though the single multiplexer chip 46 is illustrated in FIGS. 2B and 2C, more multiplexers can be used.

Also, the (reduction) ratio between transducer elements and wires can be increased to further reduce the number of wires within the catheter shaft 12, and thus reduce the catheter diameter. Alternatively, multiplexers are used to increase the number of transducer elements on an 8 F to 10 F catheter for greater than 64 transducer elements using 64 electrical wires. Each transducer directly connects to an electrical conductor/wire on a flex circuit before the multiplexer. For example a 256 element transducer array can be configured as a 1×256 linear array, a 2×128 1.5D array or alternatively as a 16×16 array for 3D imaging. A catheter with an array configured for 3D or three-dimensional imaging has the ability to be used in 3D applications, for example to guide a "smart" ablation or other therapeutic procedure to a specific point or area in a 3D map. By placing in the tip 34 a tracking device such as a wire loop or RF antenna for determining, positioning, and tracking the position and orientation of the catheter tip, a three dimensional map or image of the entire area of study can be obtained. The coordinates of the catheter tip 34 are downloaded and combined with multiple "slices" or frames of ultrasound image data.

Figure 2D:
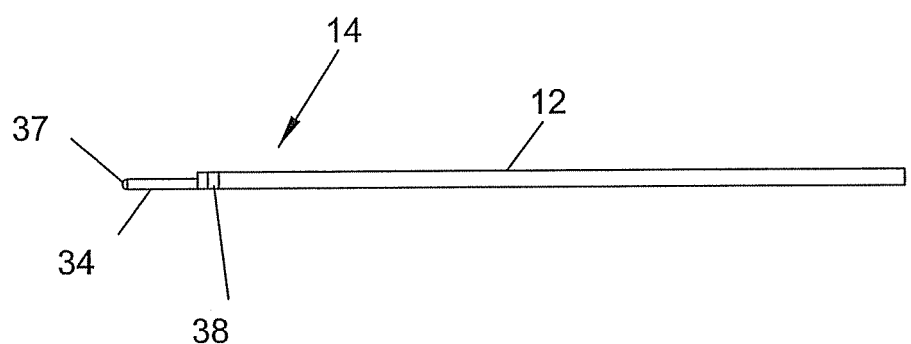
FIGS. 2D and 2E are illustrations of a flexing steering mode of an ICE catheter.
Figure 2E:
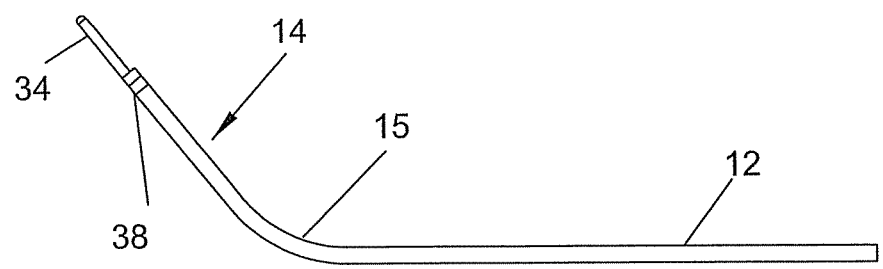

FIGS. 2D and 2E illustrate distal segment 14 flexing steering affected by the second actuator 24 in the first embodiment. The catheter 12 is flexed, using the actuator 24, from a straight configuration as illustrated in FIG. 2D into a flexed steering configuration, as illustrated in FIG. 2E. In addition, the catheter 12's distal segment 14 is steerable into any number of flexed positions in between the straight configuration of FIG. 2D and the flexed configuration of FIG. 2E, and can even be flexed beyond the configuration of FIG. 2E. The catheter is capable of flexing past the 90° point in each direction and has an angular range of 0° to 150° from the straight or neutral configuration. The second direction is similar to what has been illustrated in FIG. 2E, and it can be appreciated that it is simply the mirror image of the configuration of FIG. 2E illustrated for the first direction.

To affect flexing the distal segment 14 in the manner described above, the second steering actuator 24 (e.g., knob) is turned in a first rotational direction with respect to the relatively fixed position handle 18. Rotating the actuator 24 in the first direction causes a first steering wire 56 (see, e.g., FIG. 8) to apply tension to a steering bulkhead 38 forcing the distal segment 14 of the catheter shaft 12 to bend at bending joint 15 (see, FIG. 2E). In order to flex the catheter in the opposite direction, the second steering actuator 24 is turned in an opposing second rotational direction with respect to the handle 18. This causes second steering wire 58 to apply tension to an opposite side of steering bulkhead 38, forcing the catheter to bend in an opposite direction at the bending joint 15. The catheter assembly 10, by way of example, supports bidirectional flexed steering by at least 150 degrees in each direction from a neutral or straight catheter position. Using the combination of these two steering modes (rotational and flexing) is much more intuitive to the user than a steering mechanism based solely on either rotation or flexing—but not both. In an example of a method for using the catheter assembly 10 having both rotational and flex steering, the catheter tip 34 is first placed into a desired location of the body, for example the right atrium of the heart. While visualizing the catheter tip position 34, such as with ultrasound or fluoroscopy, the second steering actuator 24 is adjusted until the catheter orientation is close to the desired orientation. The first steering actuator 22 is then adjusted so that the rotatable tip 34 points the transducer array 32 in the desired orientation for the target image plane.

Figure 9:
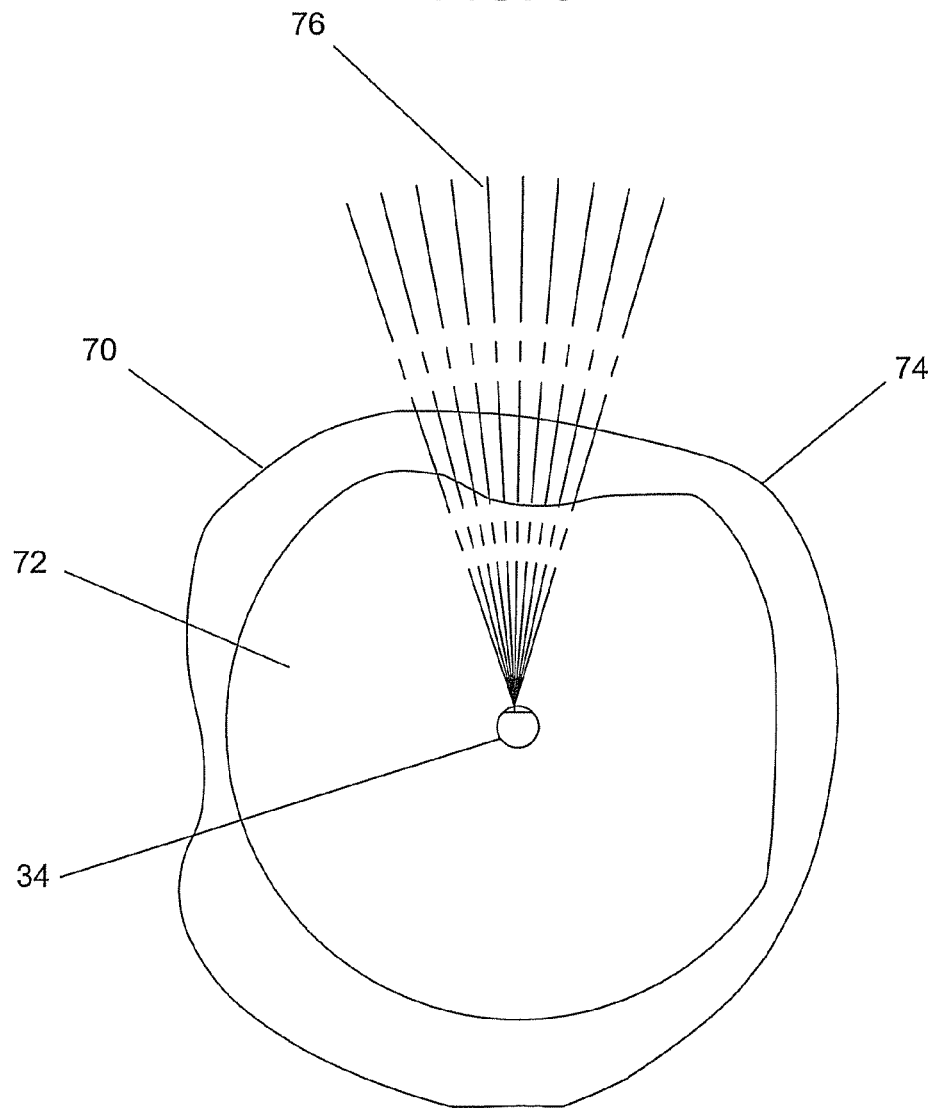
FIGS. 9 and 10 illustrate a rotational steering catheter being used to image structures in the heart.
Figure 10:
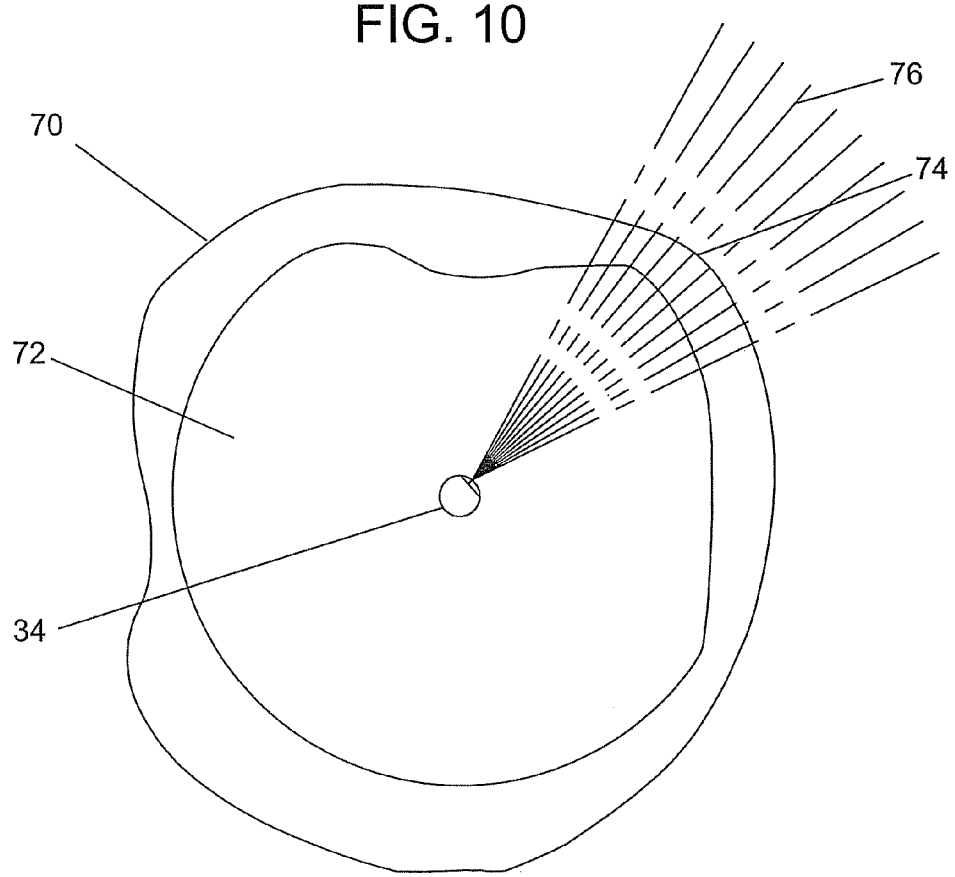

FIG. 9 illustrates the rotatable catheter tip 34 in place in a right atrium 72 of the heart. Second steering actuator 24 has already been adjusted to orient the catheter tip 34 in the correct tip flex position. As illustrated in FIG. 9 the desired structure to be imaged, an atrial septum 74, is not being imaged by ultrasound waves 76. A heart wall 70 is instead being imaged. By manipulating first steering actuator 22, the rotatable tip 34 is turned so that the ultrasound 76 impinges on the desired structure. This is done without torquing/twisting the catheter shaft 12. In FIG. 10, the adjustment of first steering actuator 22 is complete, and the rotatable tip 34 is now in position to image the atrial septum 74.

Figure 18:
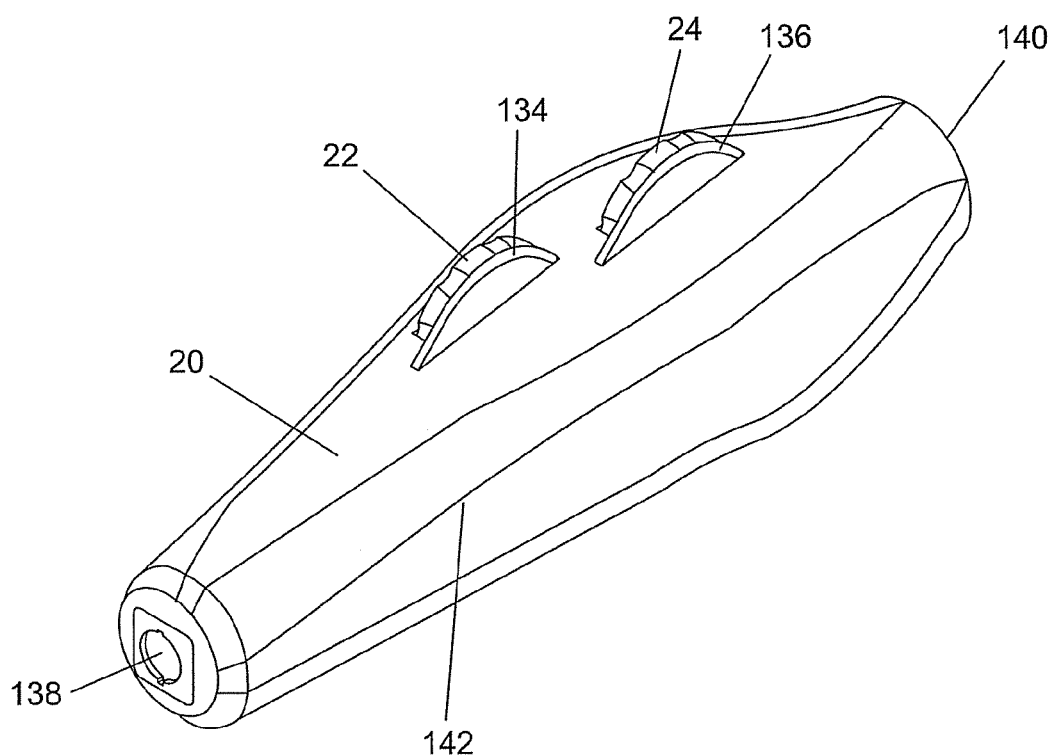
FIG. 18 is a detailed illustration of a catheter handle.

FIGS. 3-8 and 18-21 illustrate detailed construction of the catheter assembly 10 of the first exemplary embodiment. FIG. 18 illustrates the handle 18 with the catheter shaft 12 and the strain relief 26 removed to show a proximal orifice 138. Cable wires 28 from the connector 30 extend through a proximal orifice 138. The catheter steering mechanisms and signal wire bundle extend through distal orifice 140.

It can be seen that the contour of the handle facilitates one-hand use. The lower portion of the thumb and the two smallest fingers comfortably grip the handle 18 at a grip area 142. The shape of the handle 18 and positioning of the actuators 22 and 24 permits easy access for the thumb on the top of the handle and either the index or middle finger on the bottom of the handle to manipulate either the first steering actuator 22 or the second steering actuator 24 while maintaining hold on the grip area 142 of the handle 18.

Figure 19:
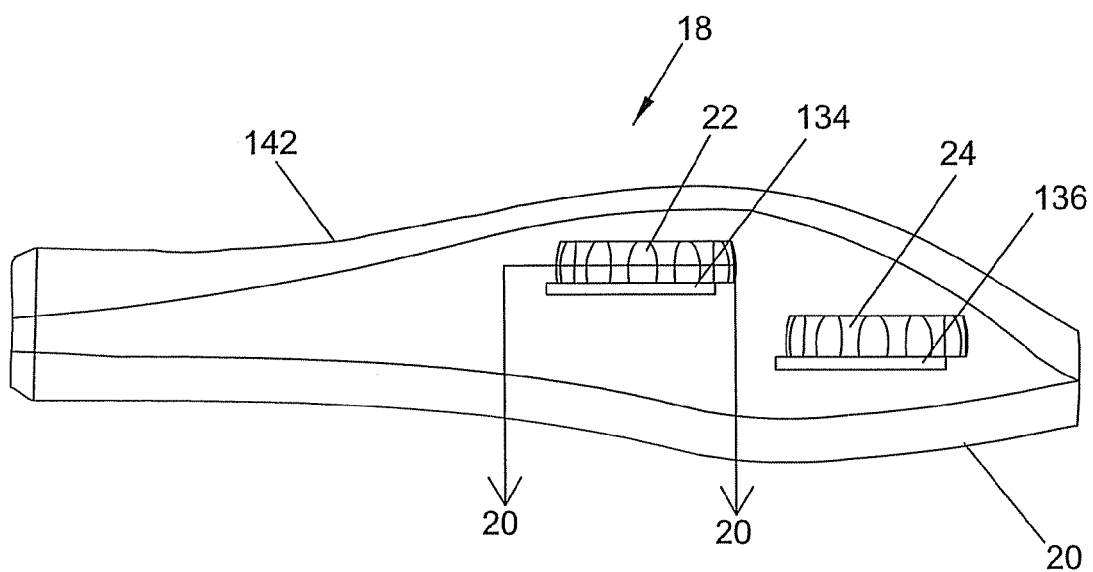
FIG. 19 is a top view of the same catheter handle.

FIG. 19 illustratively depicts a top view of the handle in FIG. 18 to more clearly show the offset (staggered) alignment of the two actuators 22 and 24 with regard to a shared surface of the handle 18's housing 20. With continued reference to FIG. 18, a first lock lever 134 and a second lock lever 136 protrude slightly above the outer edges/diameters of the first steering actuator 22 and second steering actuator 24. While in the resting locked position shown, the locking mechanisms controlled by the levers 134 and 136 do not allow the actuators 22 and 24 to be moved, thus maintaining the catheter 10 in its desired rotational and flex state. While a user's thumb manipulates one of the actuators 22 and 24, the associated one of the lock levers 134 and 136 is held down slightly by the thumb, releasing the corresponding locking mechanism and allowing the actuator to be moved (e.g., the knob rotates).

It can be seen from FIG. 18 that the contours of the actuators 22 and 24 and lock levers 134 and 136 are configured so that it takes a small amount of force to hold the lock levers 134 and 136 down, and the thumb slides easily over the lock lever 134 and 136's surface while moving the corresponding actuator 22 or 24. After the actuator 22 or 24 is moved to the desired position and the thumb is taken off the lock lever 134 or 136, the corresponding lock automatically engages the actuator 22 or 24, holding the actuator 22 or 24 in the desired position until the next time it is to be moved.

Figure 20:
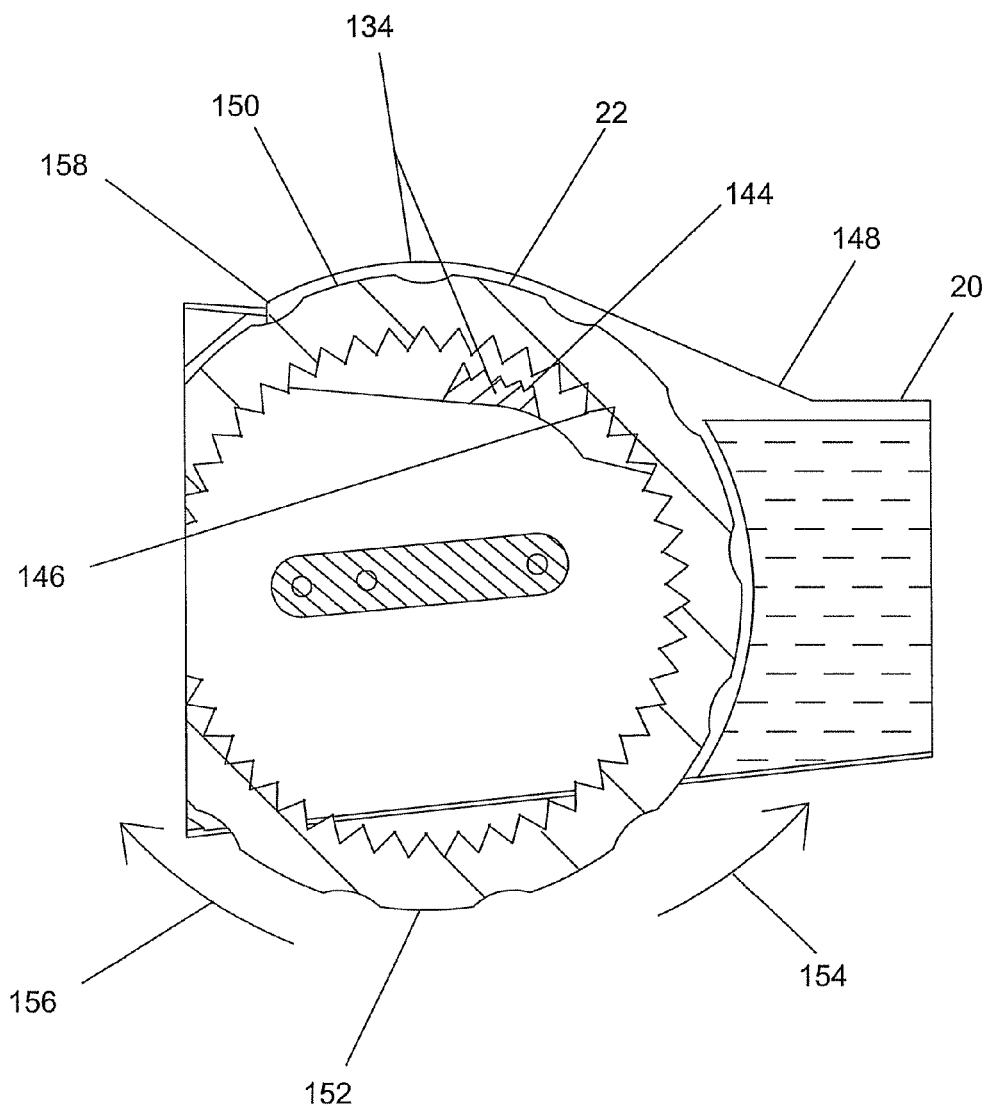
FIG. 20 is a cross-sectional view of the locking/unlocking mechanism in one of the knobs of the catheter handle.

FIG. 20 illustrates an exemplary configuration for the locking mechanism on the actuator 22 (taken along section line 20 in FIG. 19), though other configurations such as a clutch (see, e.g., FIGS. 24 and 24A described herein below) are contemplated in alternative embodiments. The first lock lever 134 is attached at one end to the handle 18 and has a free floating lock lever end 158 at the other end. The first lock lever 134 has a flexible portion 148, made, for example from a flexible polymer that is within its elastic limit over the flexible locked/unlocked displacement range used in the locking mechanism. Exemplary polymers include polycarbonate, acetal (such as Delrin® acetal resin), or any hard—yet flexible—plastic.

FIG. 20 illustrates the lock 134 in an unlocked position in the handle 18. Note an upper thumb surface 150 and a lower finger surface 152. The first lock lever 134 contains lock teeth 144, which, when in the unlocked position, are not engaged with steering knob teeth 146. In this position while the first lock lever 134 is held down and the flexible portion 148 is flexed, the first actuator 22 is turned to the desired orientation or angular position. When the first lock lever 134 is released, lock teeth 144 engage with steering knob teeth 146 and the first actuator 22 is locked in its angular position.

Though the embodiment shown in FIG. 20 utilizes the engagement of teeth as an actuator locking mechanism, in an alternative embodiment the teeth locking mechanism is replaced by a friction surface on the lock that when engaged to a surface of the actuator (e.g. the wheel), the friction surface creates a holding force. The friction on the steering actuator's surface can be created by using a rough surface, or an elastomeric material like silicone, thermoplastic elastomers or rubbers, or a tacky material. In addition, though a radial engagement of the locking mechanism is shown, alternatively, the mechanisms as described can be incorporated in the axial direction.

Figure 24:
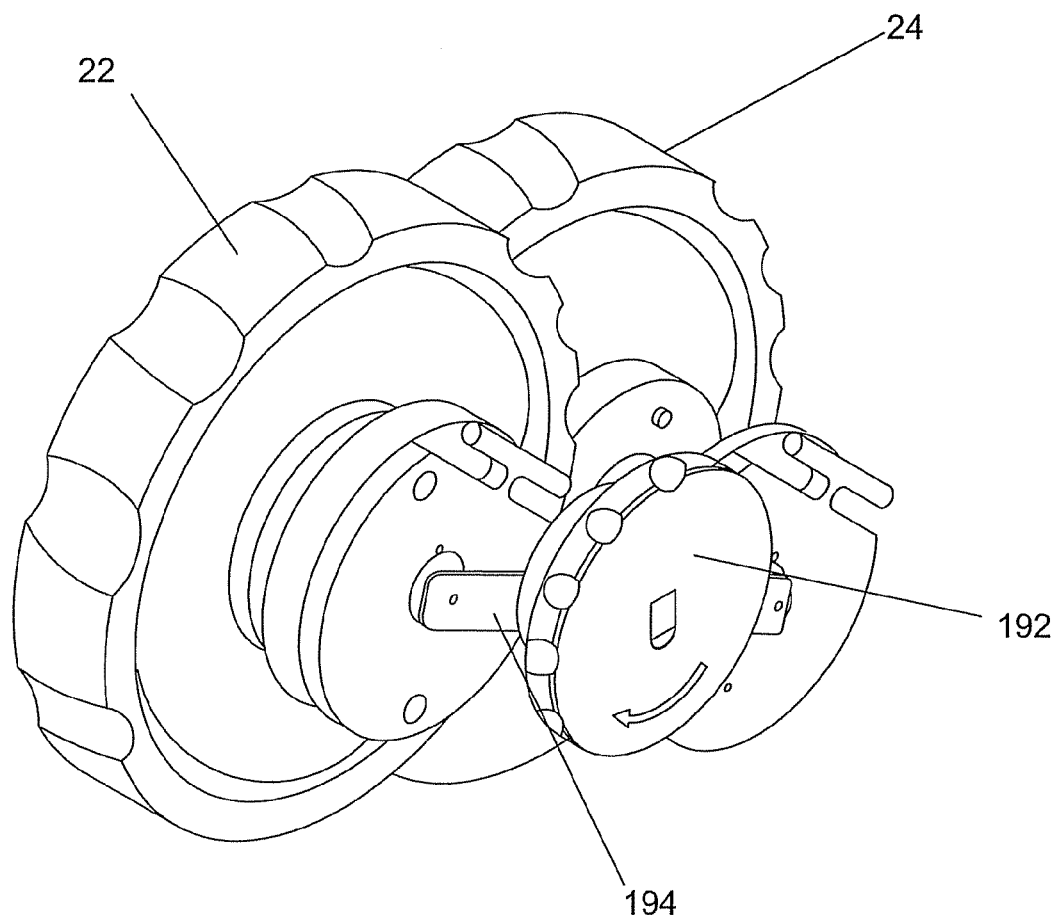
FIGS. 24 and 24A is a detailed view of a clutch in relation to the knobs.
Figure 24A:
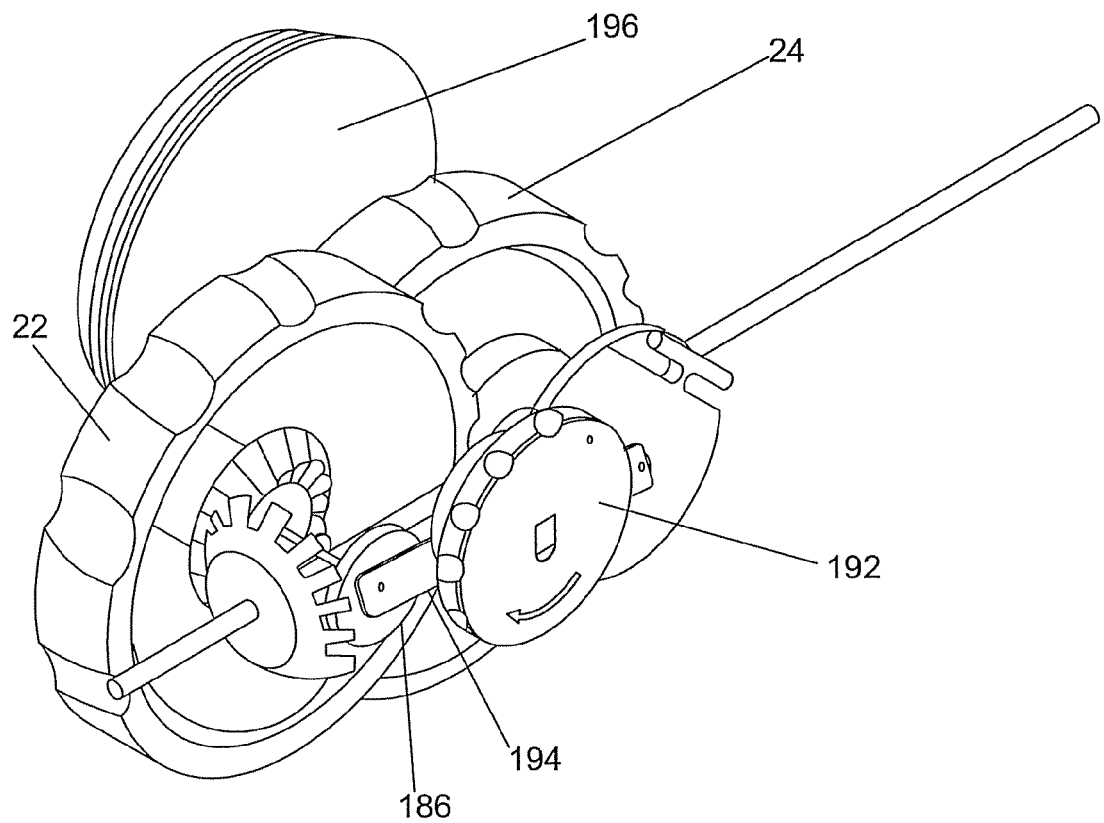

Alternatively, referring to FIGS. 24 and 24A, the locking mechanism is provided by a clutch that includes a tensioning knob 192, a friction cone 196 and the actuators 22 and 24. The tensioning knob 192 generates a lateral displacement pushing the actuator 24 into further contact with the friction cone 196 resulting in a greater level of resistance to rotational motion. A similar cone (not shown) exerts resistance on the actuator 22. The controllable additional resistance provides greater controllability to hold the actuators 22 and 24 against the restoring force presented by the steering lines that are in tension to maintain a desired position of the transducer probe mounted on the rotatable tip 34.

Figure 3:
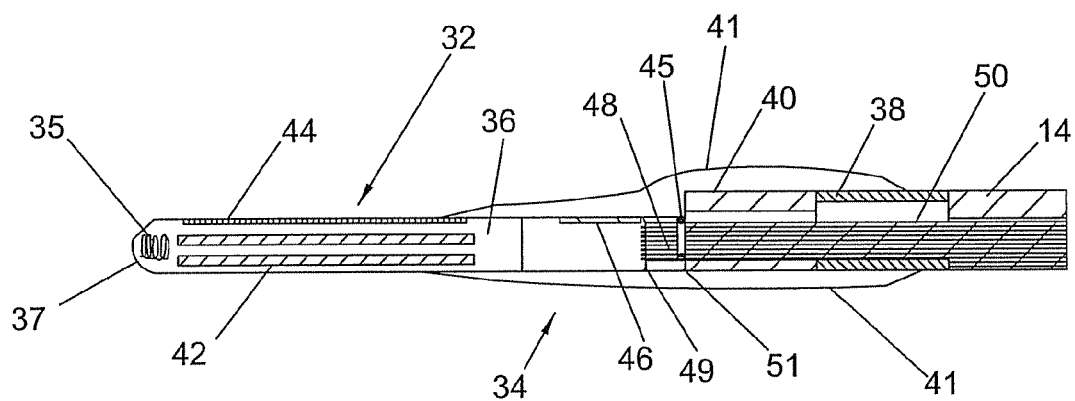
FIG. 3 is a section taken along line 3 in FIG. 2.
Figure 4:
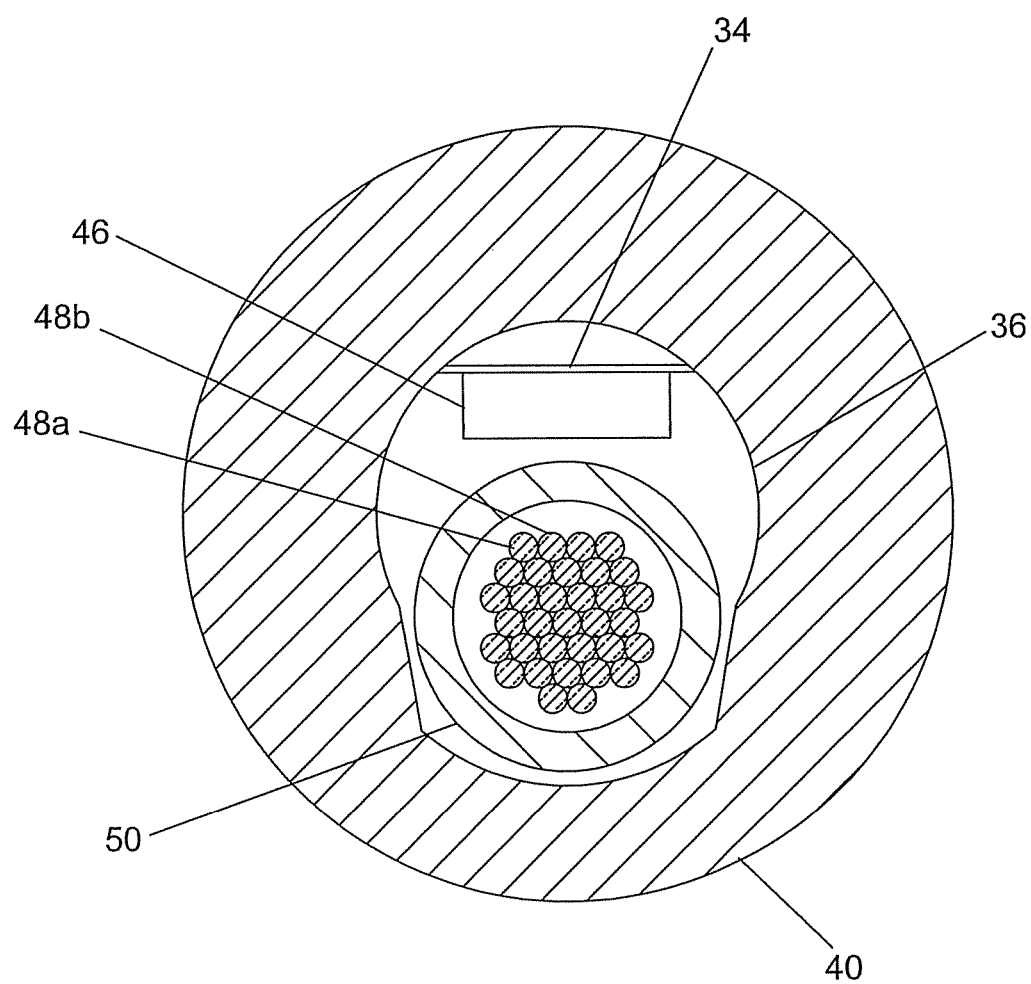
FIG. 4 is a cross-section taken along line 4 in FIG. 2.
Figure 5:
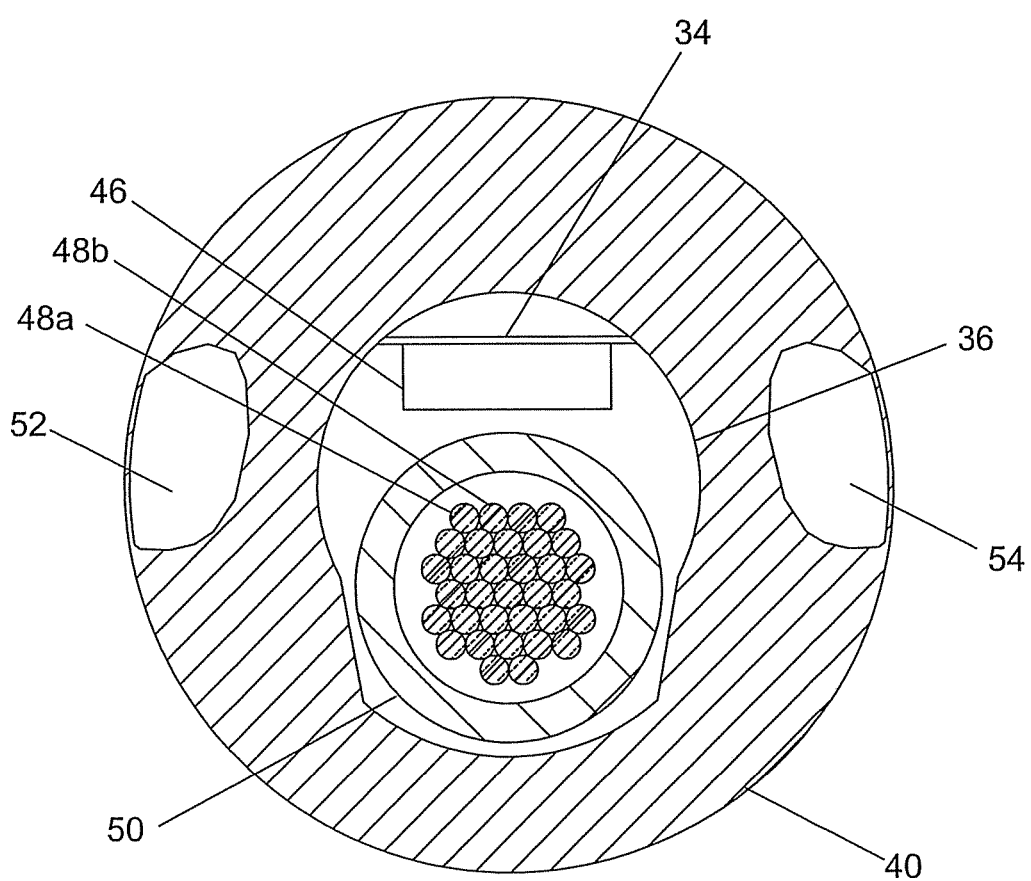
FIG. 5 is a cross-section taken along line 5 in FIG. 2.

FIG. 3 illustrates an exemplary embodiment of the rotatable tip 34. The rotatable tip 34 has a length that typically is 10 mm, and ranges from 5 mm to 20 mm. The exemplary transducer array 32 includes 64 transducer elements 44 mounted on a backing material 36. Inside the rotatable tip 34 is a stiffening member 42 proximate to the transducer elements 44. The stiffening member 42 can be a tube or rod, or can be of noncircular cross-section. Stiffening member 42 is made, for example, from a stiff material, such as a metal. The stiffening member 42 is made, for example, of a radiopaque metal, such as platinum, though stainless steel of sufficient wall thickness is sufficiently radiopaque. Alternatively the transducer array 32 is large and stiff enough on its own, so that the stiffening member is not needed.

The chip 46 is shown and provides for multiplexing, signal amplification or a combination of both as described earlier. A rotation point 51 represents the portion on the rotatable tip 34 that interfaces with the distal segment termination 40 on the distal segment 14 of the catheter shaft 12. The distal segment termination 40 is made, for example of engineered nylon (such as Pebax® polyether block amide). Attached to the rotatable tip in this embodiment is a torque member 50, made of a torquable tube, for example a braided or coil reinforced tube. It can also be made from a co-extruded tube. This tube can also act as electromagnetic interference (EMI) shielding. A cable bundle 48 is shown inside the torque member 50. The cable bundle 48 can be coaxial or simple wire, etc. Each of the cables of the cable bundle 48 is terminated to electrical connections 49 interfacing with the integrated circuit chip 46.

As FIGS. 3-8 illustrate, when the first steering actuator 22 is moved, end piece 40, steering bulkhead 38, and catheter shaft 12 remain rotationally static, but torque member 50, cable bundle 48, and rotatable tip 34 all rotate together to the desired angular position.

To prevent blood from entering the central lumen 47 of the catheter shaft 12, a seal 45 such as an O-ring seal is placed at the rotation point 51 that allows the rotating components to rotate but serves as a barrier for blood to enter. In addition, a flexible sheath 41 connects and covers the tip 34 and distal segment 14 of the catheter 12 and provides for the tip 34 to rotate bidirectionally relative to the distal segment 14 by at least 360 degrees in each direction. In addition the sheath 41 provides a seal for the tip and distal segment of the catheter 12 from bodily fluids. The ends of the sheath 41 are thermally joined/fitted to the tip 34 and distal segment 14 of the catheter 12 to form a seal.

Figure 21:
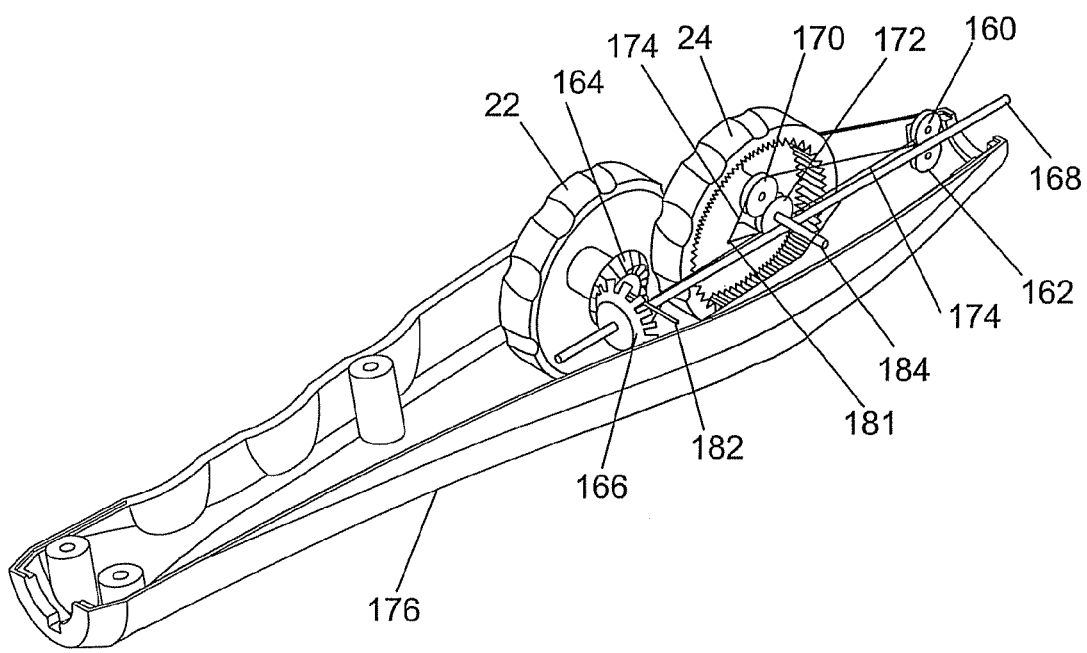
FIG. 21 is a detailed internal view of a first embodiment of the catheter handle for use with a catheter having a combination of rotational steering and flexed steering.

FIG. 21 is a detailed internal view of the first embodiment of the catheter handle 18 for use with a catheter having a combination of rotational steering and flexed steering. FIG. 21 illustrates a gearing interface that enables the first actuator 22 to turn torque member 50, which turns the cable bundle 48 and the rotatable tip 34. The lock levers and top housing half of handle 18 are not shown in order to more clearly illustrate the gearing interface.

The first actuator 22 is rotated around a first shaft 182 causing actuator gear 164 to turn shaft gear 166. Shaft gear 166 is attached to a stiff torque shaft 168, which torque shaft is in turn attached to the torque member 50 in the catheter shaft 12. Alternatively, the torque member 50 is directly attached to shaft gear 166. As illustrated in FIGS. 20-21, when the first actuator 22 is rotated in a first rotational direction 154, the stiff torque shaft 168 is rotated clockwise. When the first actuator 22 is rotated in a second rotational direction 156, the stiff torque shaft 168 is rotated counter-clockwise. Though a beveled gear pair is illustrated, alternatively other gearing mechanisms can be used, such as a worm and wheel combination.

Figure 8:
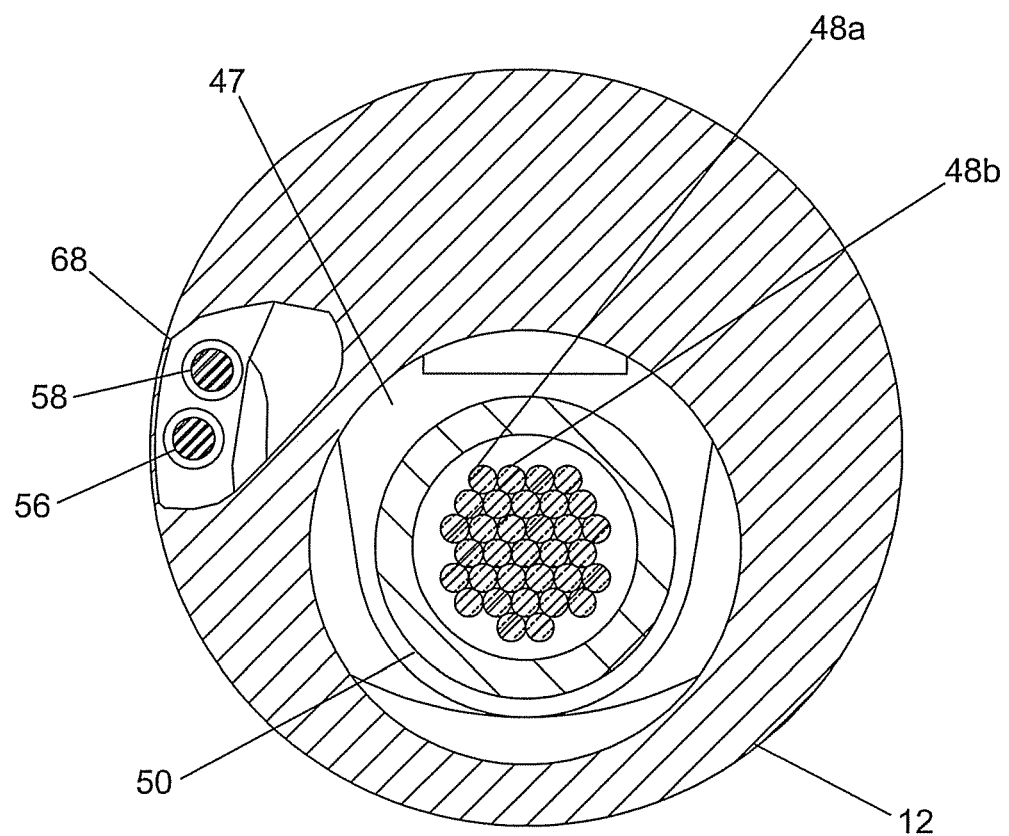
FIG. 8 is a cross-section taken along line 8 in FIG. 2.

FIG. 8 illustrates a cross section of the catheter shaft 12 over the majority of its length. The catheter shaft 12 includes central lumen 47 containing the wire bundle 48 including individual wires (e.g., 48a and 48b) and a shared lumen 68 through which the first steering wire 56 and the second steering wire 58 pass. Each steering wire can alternatively be within its own sheath (not shown), and both assemblies of wire and sheath are contained within the shared lumen 68.

Figure 7:
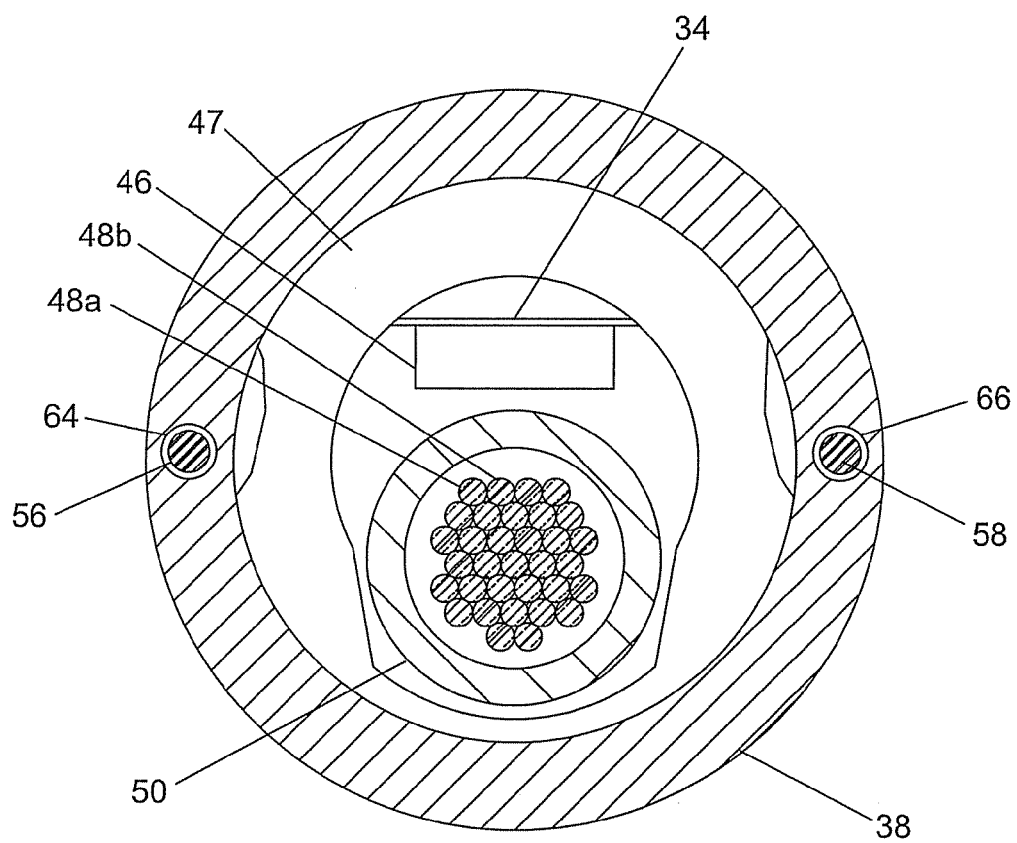
FIG. 7 is a cross-section taken along line 7 in FIG. 2.

Further distal, as illustrated in FIG. 7, the catheter shaft 12's configuration at steering bulkhead 38 includes a cross section having central lumen 47, as well as first steering lumen 64 and second steering lumen 66, through which the first steering wire 56 and the second steering wire 58 pass individually. In between the proximal and distal ends of the catheter 12 having exemplary cross sections illustrated in FIGS. 8 and 7, the assemblies of wire and sheath transition from the shared lumen 68 to the separate steering lumens 64 and 66.

Figure 6:
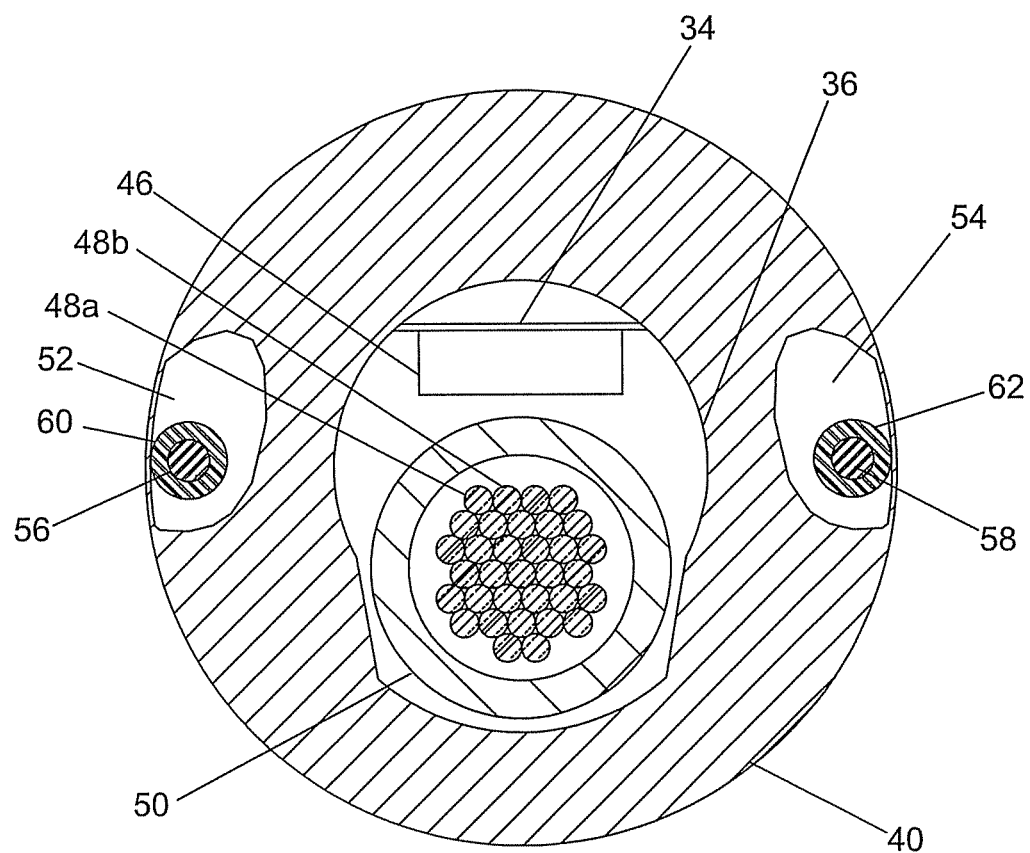
FIG. 6 is a cross-section taken along line 6 in FIG. 2.

FIG. 6 shows the portion of the distal segment termination 40, at which the distal ends of both of the steering wires 56 and 58 are located. Steering wires are alternatively called steering lines. Attached or secured to the ends of the steering wires are a first end cap 60 and a second end cap 62. As an alternative method to connect and attach or secure the steering wire to the distal segment of the catheter, a single steering wire turns around at the end piece 40, secures to the distal ends of the steering lumens by tension and adhesive for example, and runs continuously and bidirectionally inside the catheter shaft 12 from a steering control actuator on the handle 18 without using end caps 60 and 62 to accomplish flexed steering. This configuration can be repeated to enable flexing in two or more directions. The end caps 60 and 62 or alternatively the continuous loop steering wire are attached to the distal segment termination 40 using adhesive, solder, welding, brazing, swaging, crimping, or other attachment methods. The steering wires 56 and 58 are made, for example, of stainless steel or nitinol, but can also be made of aramid fiber (such as Kevlar® aramid fiber) or other high tensile types of line, and thus, the steering wires 56 and 58 are more generally called steering lines to include a wide variety of metal and non-metal materials. A first clearance lumen 52 and a second clearance lumen 54 allow the end caps 60 and 62 to fit within them, but alternatively the clearance lumens 52 and 54 can be formed permanently around the end caps. The diameter of each end cap 60 and 62 is larger than the diameter of each steering lumen 64 and 66.

By pulling the first steering wire 56 in a proximal direction, the end cap 60 impinges on distal segment of the steering lumen 64 of the steering bulkhead 38, causing this side of the catheter tubing to be stressed, thus causing the catheter shaft 12 to flex in a direction favoring this stress. Since steering wires 56 and 58 are integrally connected and wrap around a steering knob, when the first steering wire 56 is pulled, the second steering wire 58 is extended on the other side of the catheter shaft 12, resulting in a complimentary relaxation in the compliment wire and a smooth catheter profile for flexed steering. When second steering wire 58 is pulled instead of first steering wire 56, the opposite occurs and the catheter shaft flexes in the opposite direction.

In the catheter shaft as illustrated in FIGS. 3, 6-8 the cable bundle 48 that includes wires 48a and 48b has a substantially uniform diameter and radial symmetry in the wire bundle 48, such that the bending stiffness is substantially uniform in any plane or surface in flexed steering of the catheter shaft 12 in the present catheter assembly 10. The cable bundle 48 is contained in free form tubing that is soft and compliant to enable the cable bundle to fit easily and symmetrically inside a lumen or cavity. For the operator of the present system this uniform bending stiffness enables easy and accurate control for improved manipulation or maneuverability to navigate and orientate the transducers to an optimal position and orientation to image a target area in an intracardiac chamber such as an atrial chamber.

In an alternative to the configuration of FIG. 8, the shared lumen 68 is located more centrally in the catheter shaft 12. Alternatively, the steering lumens 64 and 66 pass through the central lumen 47 of the catheter 12, and there is no shared lumen. Returning to FIG. 21, an exemplary arrangement is illustrated for flexed steering of the catheter shaft 12's distal segment 14. Second steering actuator 24 is rotated around second shaft 184 causing first steering pulley 170 to rotate eccentrically and second steering pulley 172 to rotate concentrically. The knobs and steering pulleys rotate bidirectionally. First steering line 174 is wrapped around both pulleys 170 and 172 in a switch back or "z" configuration. One end of the steering line 174 terminates at an anchor spring 181 that secures to the handle.

The proximal end of first steering line 174 is secured inside the housing 20, and is attached to an anchor spring 181 to maintain tension. As the second steering actuator 24 is turned, the effective length of the first steering line 174 is changed (i.e., increasing or decreasing) depending on the direction the knob is turned. Distally in the handle 18, an upper distal pulley 160 and a lower distal pulley 162 help guide the steering line 174 as it extends into the catheter shaft 12. A second steering line is a mirror image of the first steering line arrangement already described.

Figure 25:
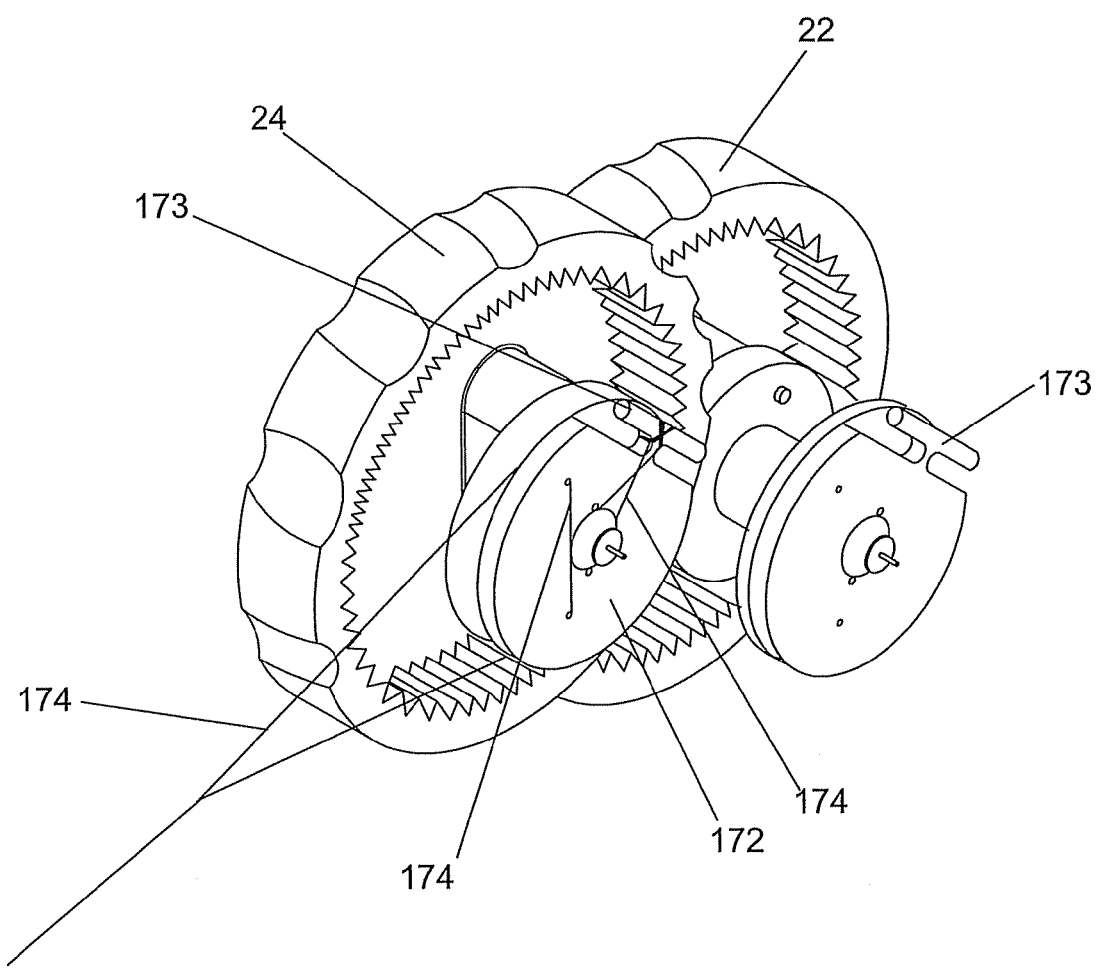
FIG. 25 is a detailed view of a cleat or tie-off mechanism attached to a knob.

As further illustrated in FIG. 25, the steering line 174 alternatively wraps around a steering pulley 172 and a cleat 173 or alternatively called a tie-off mechanism attached to the steering pulley 172 such that steering line 174 departs from the steering pulley 172 and returns to the distal segment 14 of the catheter 12. The cleat 173 provides for proper tension to be set and the reduction or elimination of slack in the steering line 174.

Figure 8A:
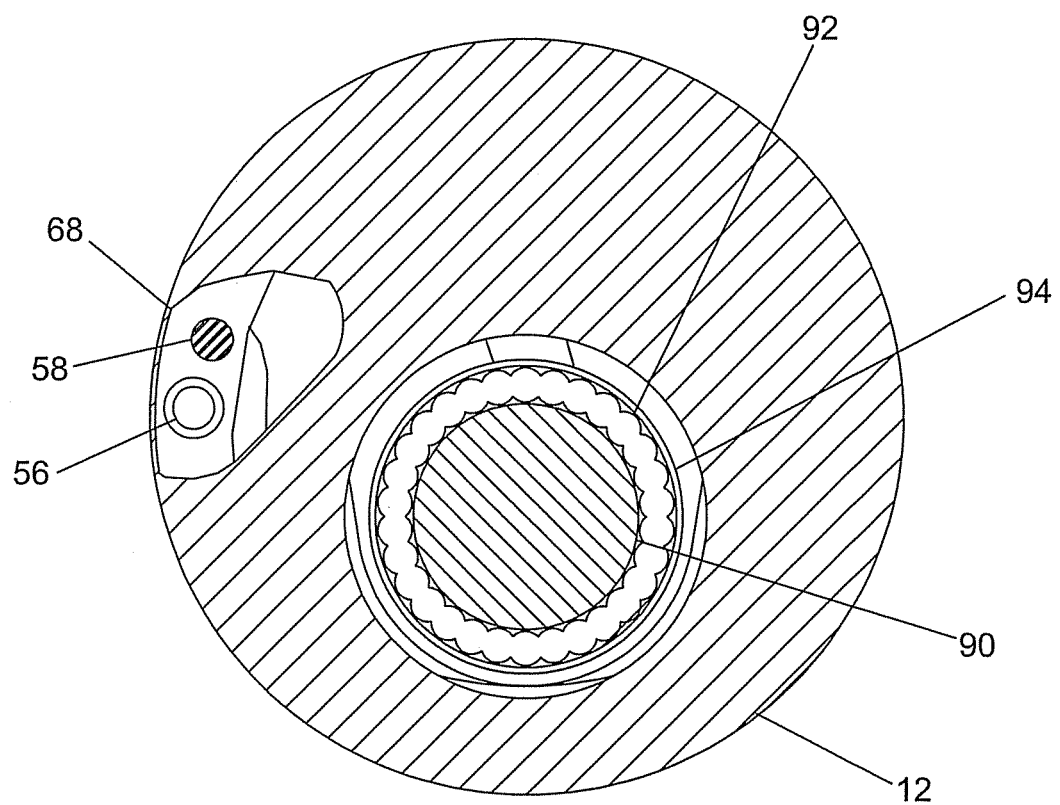
FIG. 8A is an alternative embodiment of the catheter in FIG. 8.

An alternative embodiment of the catheter assembly is illustrated in FIG. 8A. In contrast to FIG. 8, the embodiment of FIG. 8A includes a torque cable 90 which allows the conductors, shown as a flat conductor assembly 92, to be located outside the torque cable 90, not inside a lumen. The torque cable 90 is made from multiple layer multifilar coils. The advantage to this configuration is that a cable of this type can be made to be very straight and thus have a better fine torque response than a torque tube configuration. In this embodiment, the flat conductor assembly 92 can be made from a flex circuit ribbon. The conductor assembly 92 and torque cable 90 have radial symmetry in the catheter shaft such that this configuration has the advantage of substantially uniform bending stiffness in any bending plane in flexed steering as already described. A surrounding tube 94 is made from shrink tubing, and holds the entire assembly together. Another advantage to this embodiment is that the torque cable 90 can extend further into the rotatable tip 34, to secure it, and also allows for easier routing of the conductors at the tip 34 for electrical connection to the cable bundle 48. Electrical connection can be achieved by micro-welding or soldering, or other known methods.

Figure 11:
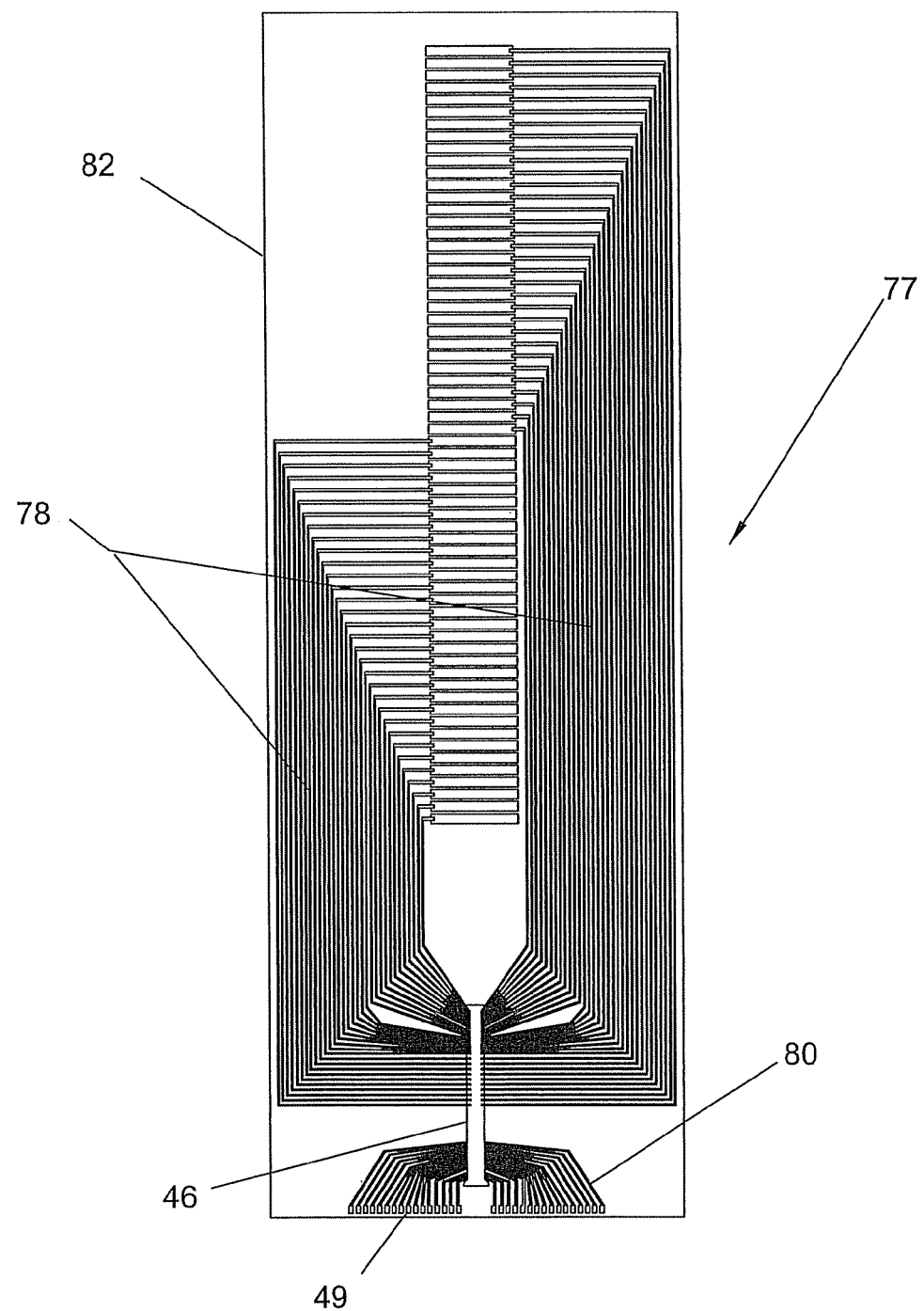
FIG. 11 is an illustration of a flex circuit for use in an ultrasound catheter.

FIGS. 11-14 illustratively depict components of an exemplary tip 34 that includes a transducer array for use in ultrasound catheters of size 6 F and smaller. FIG. 11 illustrates a flex circuit 77 component of the tip 34. In the transducer array 32 each transducer element can be independently programmed to fire. A substrate 82 is made, for example, from a thin and flexible material, such as polyimide. Some examples of polyimide are Kapton® polyimide or Upilex-S® polyimide. The substrate can also serve as an ultrasonic matching layer. Conductive tracings 78 and 80 create multiple conductors on the substrate 82 which is a part of the flex circuit. Each conductive tracing provides a single electrical conduit for each transducer.

Figure 12:
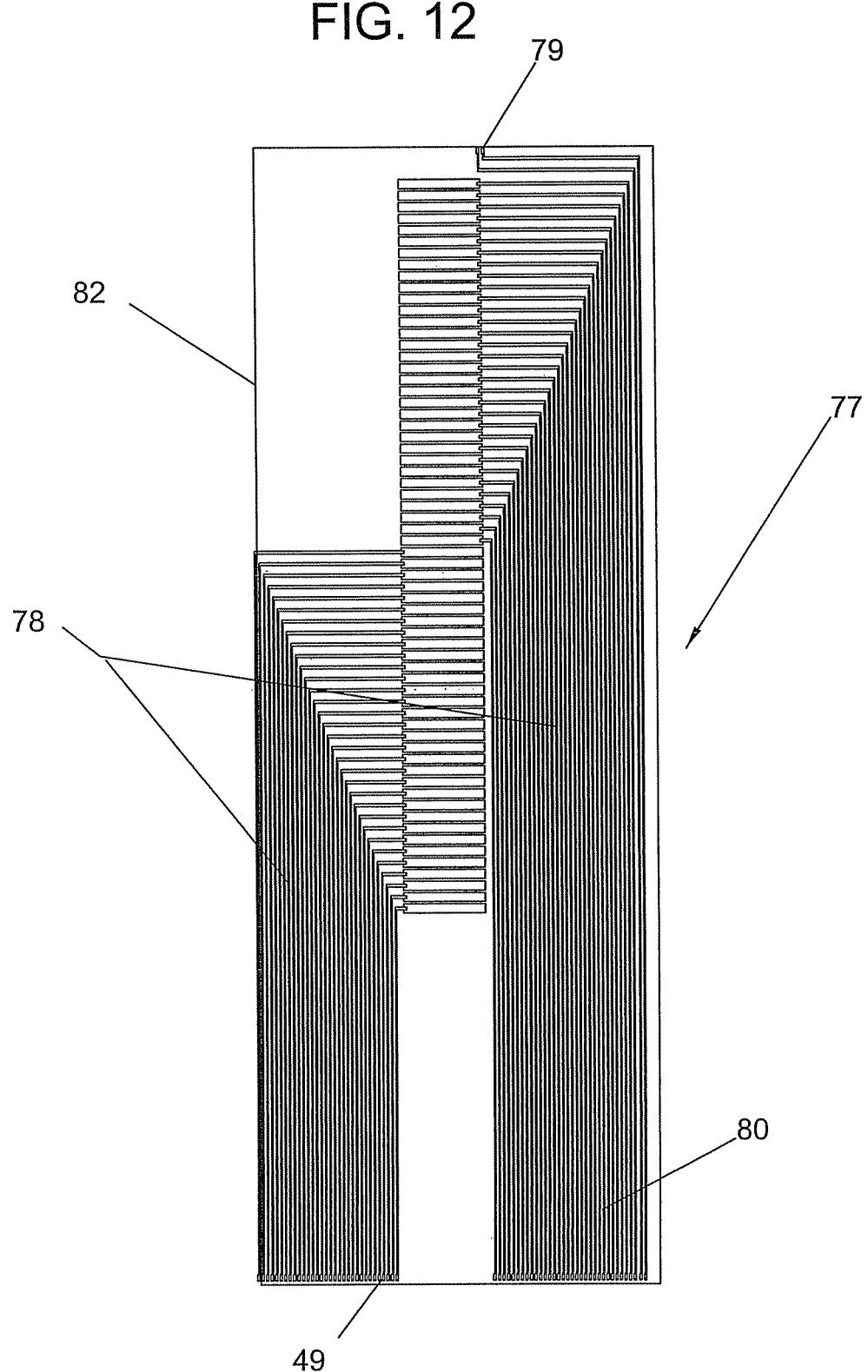
FIG. 12 is an illustration of a transducer/circuit assembly for use in a linear array ultrasound catheter.

In FIG. 12, transducer elements are attached to the flex circuit 77. In one method of fabrication, a piezoelectric material block is attached, and then kerfs are made with, for example, a dicing saw, to create the individual transducer elements. One or more integrated circuit or chip 46 is connected to the conductive tracings 78 and 80. In a specific configuration as illustrated in FIG. 12 the chip 46 is connected between the two groups of conductive tracings 78 and 80. In addition other devices such as a wire loop or RF antenna 35 (see, e.g., FIG. 3) in the tip 34 is connected to conductive tracings 78 and 80 via terminals 79. Terminals 49 allow electrical connection of the aforementioned conductive tracings 78 and 80 to the cable bundle 48. An example of a flex circuit that includes terminals 79 but no integrated circuit is illustrated in FIG. 12.

Figure 13:
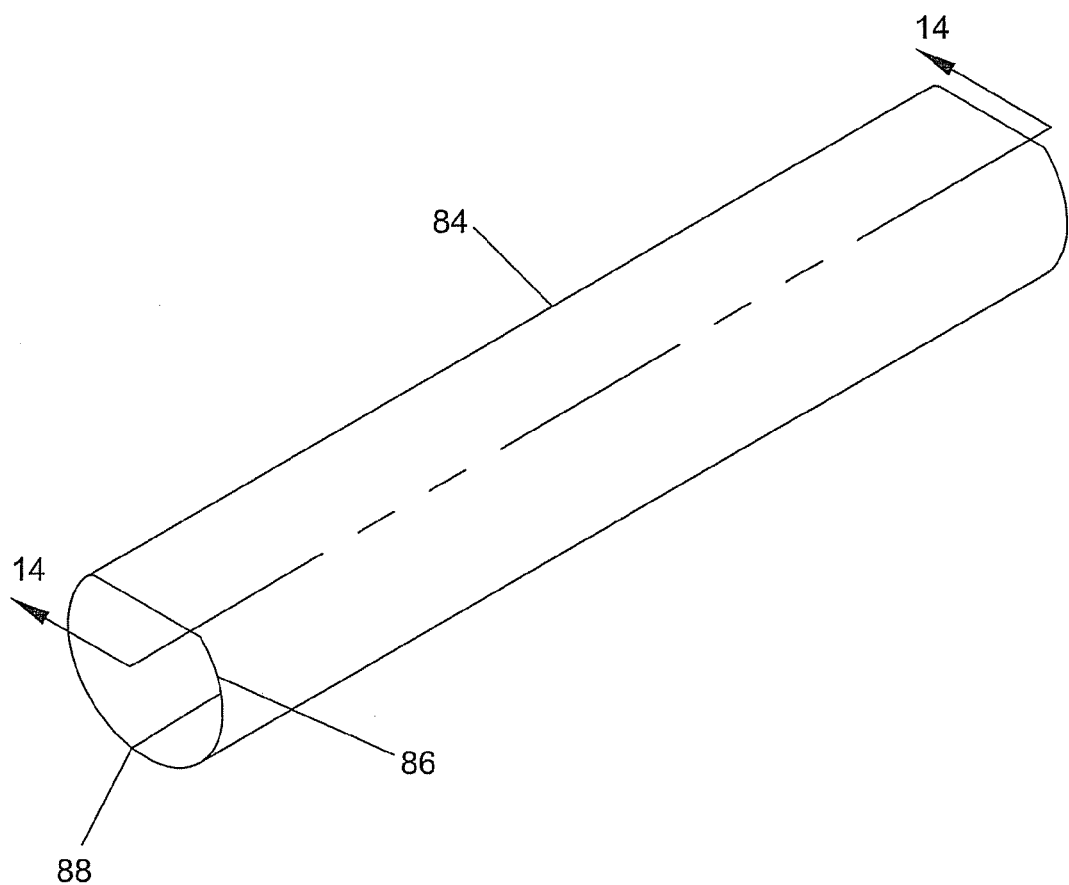
FIG. 13 illustratively depicts the transducer/circuit assembly of FIG. 12 in a rolled or wrapped configuration.
Figure 14:
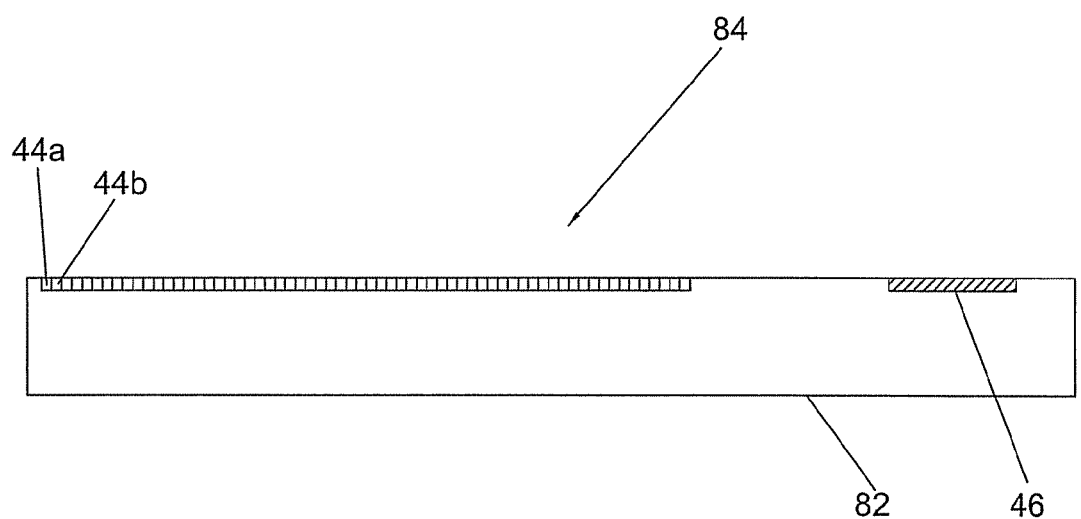
FIG. 14 is a cross-section of the rolled transducer/circuit assembly of FIG. 13 taken along line 14.

In FIGS. 13 and 14 (see also FIG. 3), the assembly of FIG. 12 is rolled into a rolled transducer assembly 84 having a D-shaped cross-section 86 and a seam 88. A distal segment of the flex circuit is rolled over a stiffening member 42 (see, FIG. 3) that is proximate to and extends alongside the array of transducers. The backing material 36 is injected inside the rolled transducer assembly 84. An additional matching layer can be formed over the assembly to provide better acoustic matching between the transducer piezoelectric material and the target tissue as well as the transmission medium. For example, RTV silicone is one such material that can be used. In one embodiment the D-shape cross section allows the linear layout of the transducer elements and uniform wall thickness of the matching layer due to the flat top for even and controlled focusing. The tip 34 has a proximal portion which has a rounded shape and encapsulates the proximal portion of the flex circuit.

Exemplary transducers for ICE have a typical thickness of approximately 0.28 mm in the piezoelectric material to enable an 8 MHz ultrasound signal to be generated and transmitted at a typical velocity of 1500 m/sec through blood. The transducer thickness can be of various thicknesses ranging approximately from 0.56 mm to 0.19 mm to generate sufficient penetration depth in tissue imaging. In general, the thickness of the transducers can be adjusted for the frequency of sound in the transmission medium for the desired penetration depth in any tissue imaging. Image intensity can be adjusted by driving voltage on the transducers.

Figure 15:
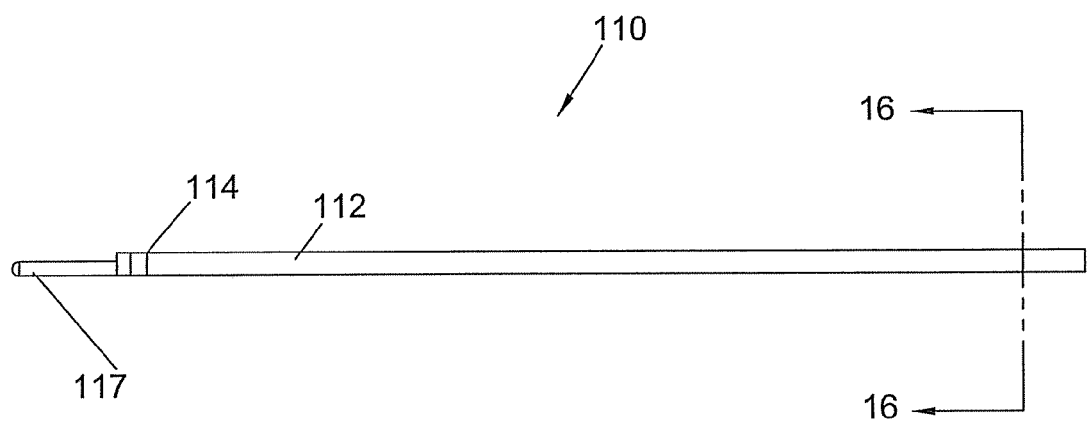
FIG. 15 is an alternative embodiment of an ICE catheter.
Figure 16:
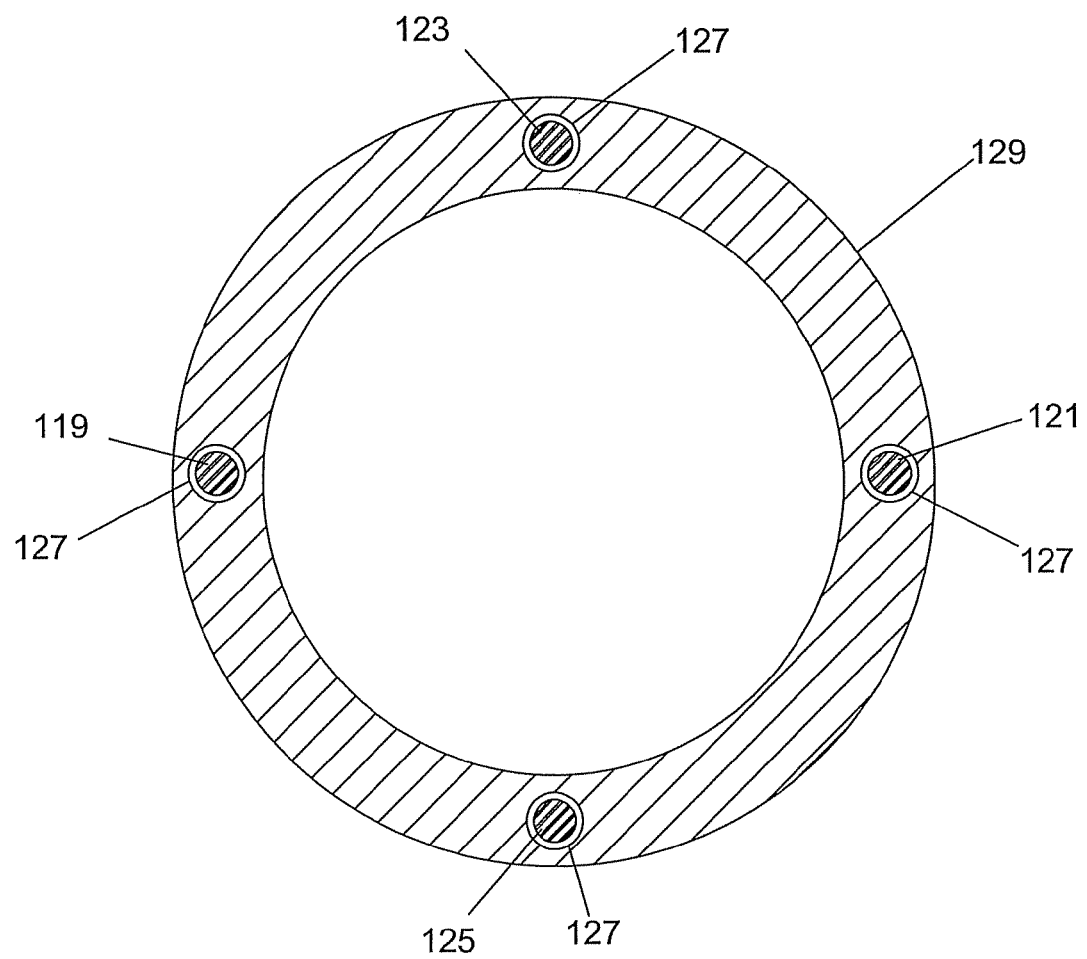
FIG. 16 is a cross-section of the catheter shaft of the catheter in FIG. 15 taken along line 16.

FIGS. 15-16 illustrate an alternative embodiment of the catheter assembly 10. Ultrasound catheter 110 includes a catheter shaft 112 and a distal segment 114 having a non-rotating tip 117. Non-rotating tip 117 has a structure similar to the rotatable tip 34 but differs in its connection with the distal segment of the catheter. Non-rotating tip 117 connects integrally to the distal segment 114 of the catheter shaft 112 and does not rotate relative to the catheter shaft 112. FIG. 16 illustrates two orthogonally arranged planar steering controls. First plane steering lines 119 and 121 and second plane steering lines 123 and 125 pass through four steering lumens in shaft 129.

In an exemplary embodiment, a two-material shaft is provided to overcome stiffness of a high lubricity material. The shaft 129 is extruded so that each lumen has a lumen liner 127 consisting of a material that is different from the material of the shaft 129. The material of the lumen liners is a high lubricity material that allows the steering lines to move axially with minimal frictional resistance. If the entire shaft were to be extruded from the material used in the lumen liners, the high stiffness of the lubricious material used would cause the shaft to be dangerously inflexible. By using an extrusion method that only incorporates this lubricious material into the lumen liners, the rest of the shaft can be made from a sufficiently flexible material to optimize catheter shaft flexibility, ease of use and safety in the patient.

Figure 17:
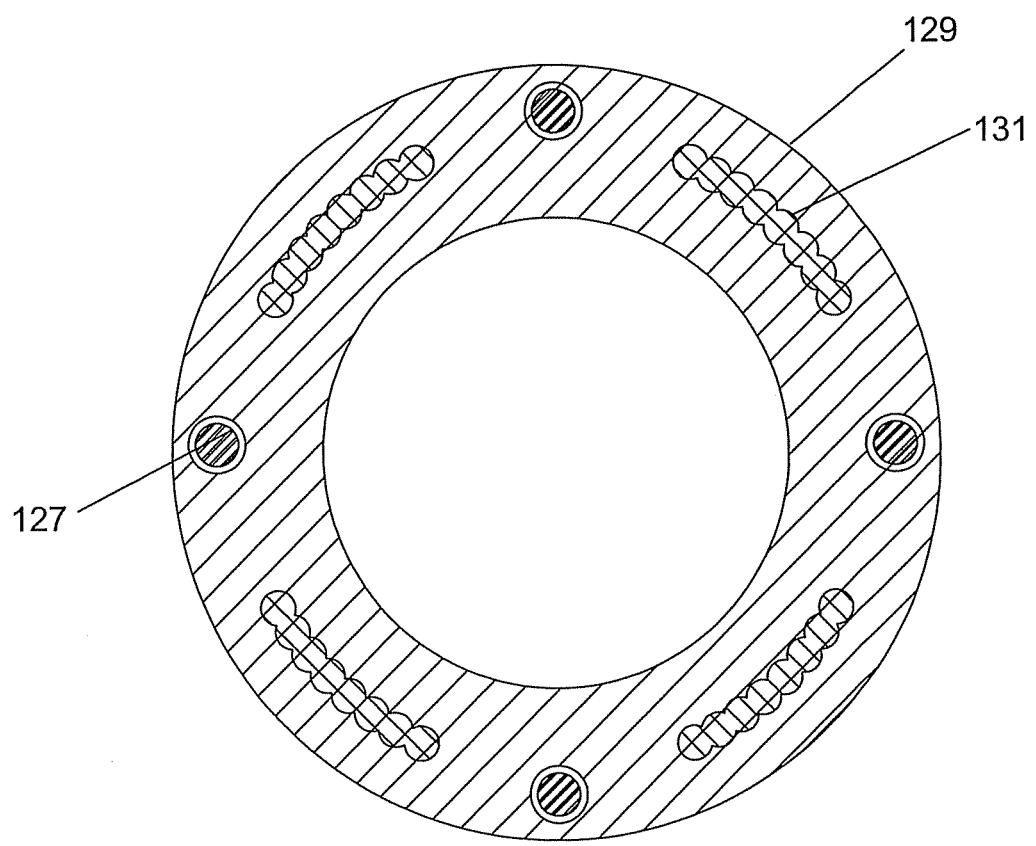
FIG. 17 is a cross-section of an alternative shaft of an ICE catheter.

FIG. 17 shows an alternative tubing extrusion that includes embedded conductors 131 within the tubing wall and extending the length of the tubing. By packaging the conductors in this manner, the wall thickness of the tubing can be increased for strength. At the distal end of the tubing the conductors are well placed for making electrical terminations and further connections to the conductive tracings of the flex circuit. As shown, a flat ribbon of several conductors can be used. In FIG. 17, four groups of eight wire ribbons are illustrated.

Figure 22:
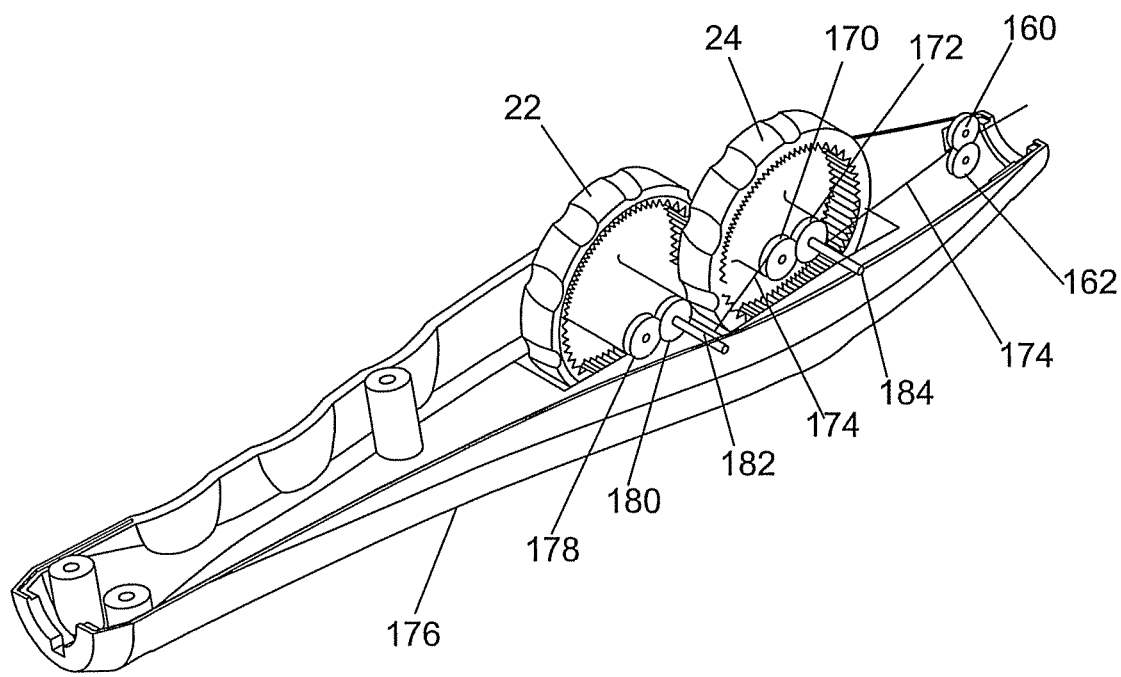
FIG. 22 is a detailed view of a second embodiment of the catheter handle for use with a catheter having two-plane flexed steering.

FIG. 22 illustrates an alternative embodiment of the handle 18 for use with the catheter embodiment of FIGS. 15-17. Second steering actuator 24 works in the same manner as that of FIG. 21. Instead of the gearing mechanism in first steering actuator 22, the embodiment of FIG. 22 contains the same mechanism in both actuators for flexed steering in two different, orthogonal, planes or surfaces. One actuator operates the catheter flexing in a first plane and the other knob operates the catheter flexing in a second plane. First steering actuator 22 operates third steering pulley 178 and fourth steering pulley 180, and its own steering lines (not shown).

Figure 23:
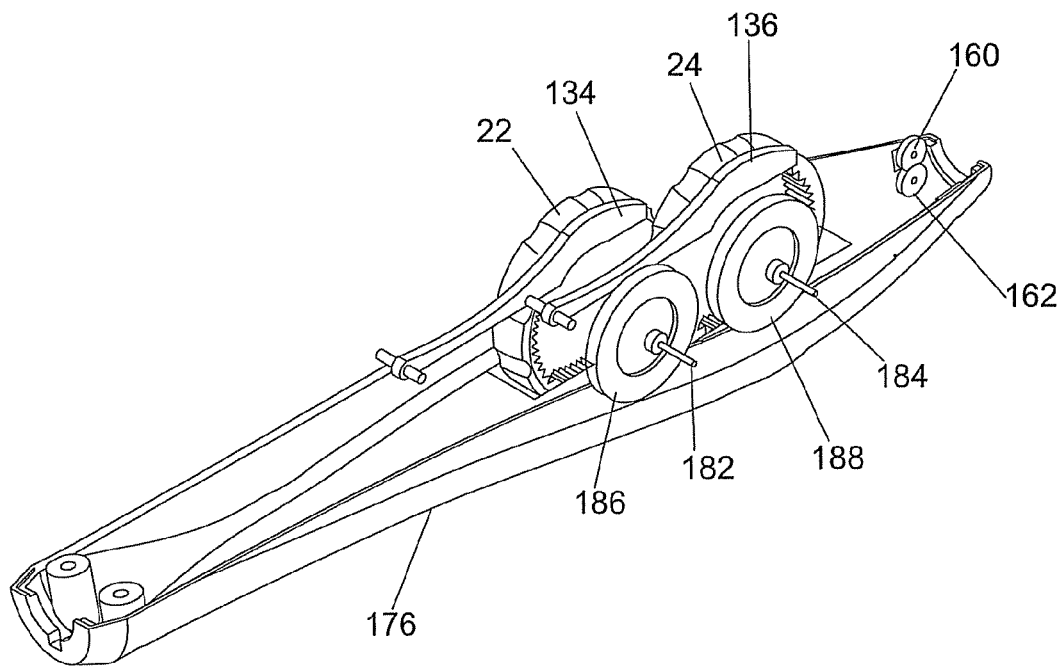
FIG. 23 is a detailed view of a third embodiment of the catheter handle for use with a catheter having two plane flex steering and showing further detail of the locking/unlocking mechanism.

FIG. 23 illustrates a similar embodiment to that of FIG. 22. In place of the two smaller pulleys in each steering knob, each steering knob instead rotates first and second large pulleys 186 and 188. For each plane, a single steering line is used from the distal end in one lumen, then proximally and around the large pulley, and then distally again, terminating at the distal end of the other lumen. The grooves of each pulley are coated with a low lubricity, high friction material, such as silicone elastomer, such that no slippage occurs on the steering line. Alternatively, the steering line is permanently attached to the pulley instead of being frictionally coupled. In this embodiment and all of the other embodiments using steering wire or steering line, tensioners (not shown) consisting of secondary pulleys spring loaded on an arm, can be used to minimize line slack.

In a third embodiment of the present system a three-way steering catheter is made that combines the two orthogonally arranged flexed steering of FIGS. 15-17 with the rotational steering associated with FIGS. 1-14. The three steering modes in this case, for example, are flexed steering left-to-right, flexed steering anterior-to-posterior, and tip rotation. An embodiment of the three plane steering catheter includes the configuration as already described in FIGS. 15-17 and adding a torque member connected to the rotating tip 14 on the distal side and to a third shaft gear assembly on the handle.

Figure 26:
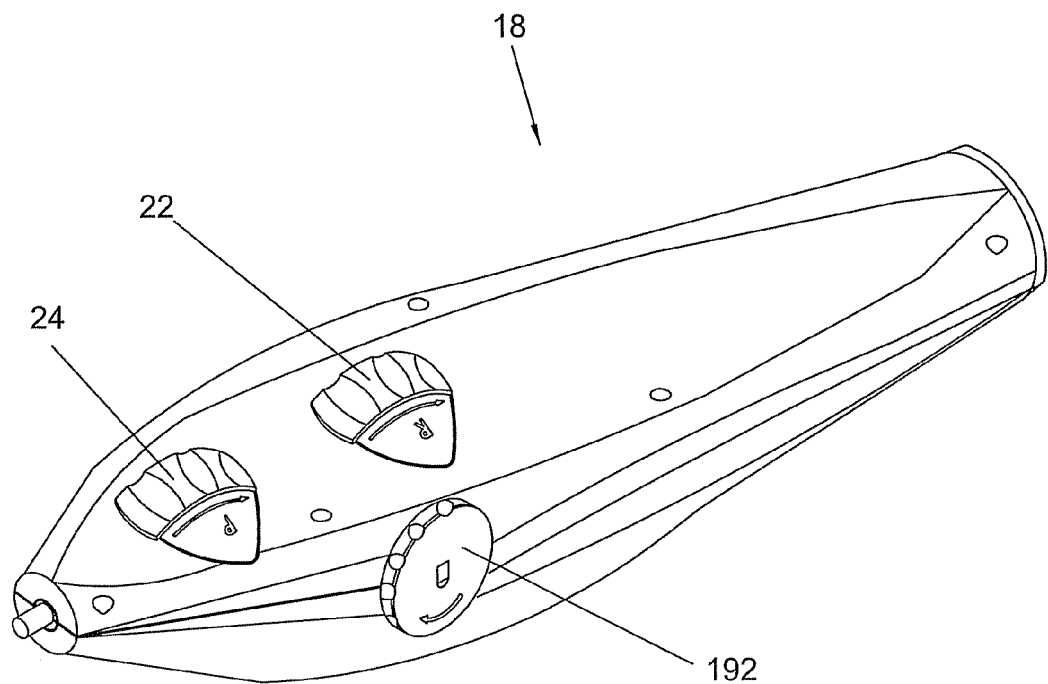
FIG. 26 is a detailed view of a handle with two knobs and a clutch.

FIGS. 24, 24A and 26 illustrate a clutch mechanism facilitated by the interaction of the following components: a tensioning knob 192, a cam 194 (or screw), actuator 24, a thrust washer 186 and a friction cone 196 (not shown in FIG. 24). Actuators 22 and 24 each are fit with friction cones (only friction cone 196 for actuator 24 is shown in the illustrative example in FIG. 24A). The thrust washer 186 acts as an interface between the cam 194 and the actuator 22. Rotating the tensioning knob 192 in a first direction results in the application of lateral displacement to actuators 22 and 24 which, in turn, increases the amount of contact area between the actuators 22 and 24 and friction cones (e.g. cone 196 for actuator 24). The increase in the contact area between the actuators and their corresponding friction cones results in increased resistance to rotational motion of the actuators—which in turn results in increased resistance to the restoring force presented by the steering lines that are in tension. The clutch mechanism acts to create a slight and variable hold of a control actuator such as actuators 22 and 24 such that an ideal position can be achieved by the clinician. By use of this variable resistance functionality the clinician can find the ideal position to do his procedure and increase the resistance to motion by further tightening the tensioning and thereby holding its set position. The resistance to movement functionality is achieved by three basic components: the friction cone 196 that is anchored to the handle 18; actuators 22 and/or 24 that have surfaces which match the angle of the friction cones and are free to turn as well as move slightly axially onto and off of the friction cone 196; and the cam 194 (or screw) that generates the side load and lateral motion of the actuators 22 and 24 onto the friction cones such as cone 196.

FIG. 26 provides an exemplary exterior view of the handle 18 including the tensioning knob 192 for applying a varying degree of resistance to movement of the actuators 22 and 24. Placing the tensioning knob 192 on a side of the handle 18 facilitates single-handed operation of the catheter assembly 10 via the exposed control surfaces of the actuators 22 and 24 and the tensioning knob 192. In alternative embodiments, the tensioning knob 192 comprises a slider external control surface that provides a variable amount of resistance to movement of the actuators 22 and 24 by moving the slider within a sliding range along the side of the housing 20 of the handle 18.

Any of the handle designs can be combined with methods for determining exactly the tip configuration of the catheter. For example, magnetic tape with circumferential position coordinates is attached to each of the two steering knobs. A multiplicative factor is included in these coordinates that transforms the circumferential displacement of the knob to either the angular displacement of the tip flex or the angular displacement of the rotatable tip rotation. A reusable magnetic reader is plugged in to the handle and the position or angular data is retrieved by the ultrasound system, or by a co-registration system coupled to the ultrasound system.

It is also within the scope of the disclosed exemplary embodiments to incorporate the improvements described into other types of ultrasound catheters, such as for example IVUS catheters. RF backscatter based tissue characterization is used in IVUS to determine plaque type (fibrous, fibro-lipidic, calcified, necrotic, etc.). This type of analysis is also known as Virtual Histology. Using this imaging technique with myocardial tissue instead of atherosclerotic plaque, different types of myocardial tissue can be identified, including for example, healthy myocardium, dead myocardium, or diseased myocardium. Also, ablated and non-ablated tissue can be identified, such as the tissue in the pulmonary veins or other cardiac tissue. RF backscatter tissue characterization can also be used to more correctly identify the extent of calcification on diseased heart valves.

An alternative steerable catheter utilizes a backbone of two-way shape memory. Current is selectively sent through different sections of a two-way shape memory metal lattice structure, causing phase change due to differential heating. For example, when current is sent through nodes on one side, the distal segment 14 of the catheter shaft 12 bends in a first direction. When current is turned off in nodes on the first side and turned on in nodes on a second side, the tip bends in a second direction, different from the first.

Another alternative steerable catheter utilizes magnetic rings. The catheter has one or more magnetic bands at the tip. When used in a laboratory equipped with a magnetic guidance system, such as that made by Stereotaxis, the distal segment 14 of the catheter shaft 12 can be made to flex in reaction to specific magnetic fields that are produced.

Another alternative steerable catheter utilizes a micromotor. Instead of the rotatable tip being rotated in one direction or the other by turning a knob manually in the handle, a motor in the handle 18 rotates the assembly by pushing either a clockwise or counter-clockwise button. Alternatively, a micromotor is embedded in the tip and when a button in the handle is pressed, the micromotor rotates the rotatable tip.

Another alternative steerable catheter tip utilizes micromachines. An articulation or microgearing system is constructed in the distal end of the catheter using nanotechnology micro parts.

Another alternative steerable catheter utilizes spinning top articulation. The distal end of the catheter shaft 12 has two opposing spiral grooves in the wall. A rotatable tip is attached to a push rod, not a torque member. The rotatable tip has two tabs, one that slidably fits into each of the grooves. When the rod is pushed, the rotatable tip rotates to the right. When the rod is pulled, the rotatable tip rotates to the left.

Another alternative steerable catheter utilizes spinning top articulation combined with piezo power. A piezoelectric material is used as a mount for a transducer array at the tip of the catheter shaft 12. By activating the mount with a voltage, the mount oscillates a few degrees (for example 10 degrees), causing the transducer array to sweep back and forth, creating a 3D image.

Another alternative steerable catheter utilizes a superelastic material. Inside the catheter shaft 12 is a shaped mandrel of superelastic material which has a sliding stiff tube over it. When the stiff tube is pulled back, the superelastic mandrel takes its curved shape. When the stiff tube is advanced, the superelastic mandrel is straightened, causing the shaft to straighten with it. The distal end of the superelastic shaped mandrel is, by way of example, flattened.

Another alternative steerable catheter utilizes a hydraulic column. A polymeric catheter shaft is pre-shaped. It contains a lumen that is filled with a material such as a mineral or vegetable oil that is nontoxic and can be sterilized. A pistoning mandrel is slidable within the lumen. At the tip of the mandrel is a sealing stopper made from, for example, a ruby or ceramic ball for ultra low friction. As the mandrel is slid distally, the ball sealably slides within the lumen, increasing the pressure of the oil within the lumen and causing a curved tube to straighten, as in a Bourdon tube. Pulling on the mandrel lowers the pressure and allows the tubing to return to its shaped configuration.

It is to be understood that the embodiments of the invention that have been described are merely illustrative of many potential applications of the disclosed device. Numerous modifications may be made to the improved ultrasound catheter that facilitates one-hand maneuvering of a steerable distal segment and tip of a catheter assembly without departing from the spirit and scope of the presently disclosed exemplary embodiments.

What is claimed is:

1. A hand-operated ultrasound catheter assembly comprising:
    an elongate flexible shaft having a proximal end and a distal end;
    an ultrasonic transducer mounted proximate the distal end;
    a set of steering lines running along the elongate flexible shaft; and
    a handle coupled to the shaft near the proximal end and adapted to steer, during an ultrasound imaging procedure, the ultrasonic transducer by applying force to actuate one or more of the set of steering lines while being simultaneously held within and manipulated by a single hand of an operator, the handle including:
        a housing having an elongate shape adapted for hand-held operation of the handle to affect steering of the ultrasonic transducer, the housing extending along a longitudinal axis between a proximal portion and a distal portion, the distal portion receiving the set of steering lines;
        a first steering actuator for controlling a position of the ultrasonic transducer, wherein the first steering actuator affects repositioning the ultrasonic transducer by repositioning a first control surface, exposed outside of the housing of the handle, of the first steering actuator lengthwise along the longitudinal axis of the housing of the handle by rotating the first steering actuator about a first shaft extending perpendicular to the longitudinal axis,
        a second steering actuator for controlling, via force applied to a steering line of the set of steering lines, the position of the ultrasonic transducer, wherein the second steering actuator affects repositioning the ultrasonic transducer by repositioning a second control surface, exposed outside of the housing of the handle, of the second steering actuator lengthwise along the longitudinal axis of the housing of the handle by rotating the second steering actuator about a second shaft extending perpendicular to the longitudinal axis; and
        an actuator locking mechanism for holding at least the first steering actuator at a current position, wherein the actuator locking mechanism comprises a locking lever extending in a direction parallel to the longitudinal axis of the housing and comprising a set of teeth for engaging a complimentary inter-locking surface on the first steering actuator;
        wherein the exposed control surfaces of the first steering actuator and the second steering actuator are staggered along a shared surface of the housing of the handle such that a longer edge of the first exposed control surface and a longer edge of the second exposed control surface extend parallel to the longitudinal axis, but are offset with respect to one another.

2. The hand-operated catheter assembly of claim 1 wherein the first steering actuator controls a rotational position of a rotatable tip upon which the ultrasonic transducer is mounted.

3. The hand-operated catheter assembly of claim 2 further comprising a torque member coupled to the rotatable tip and controlled by the first steering actuator to affect rotation of the rotatable tip.

4. The hand-operated catheter assembly of claim 3 wherein the torque member comprises a hollow inside through which a signal cable bundle passes.

5. The hand-operated catheter assembly of claim 1 wherein the second steering actuator affects flexing of a distal segment of the shaft.

6. The hand-operated catheter of claim 5, wherein the distal segment of the shaft that is subject to flexing under the control of the second steering actuator has a length between 5 cm and 20 cm.

7. The hand-operated catheter assembly of claim 1 further comprising a third steering actuator for controlling the position of the ultrasonic transducer, wherein the third steering actuator affects repositioning the ultrasonic transducer by repositioning an exposed third control surface of the third steering actuator lengthwise along the housing.

8. The hand-operated catheter assembly of claim 1 wherein a screw knob disposed outside the housing is provided to adjust a varying degree of resistance.

9. The hand-operated catheter assembly of claim 1 wherein a post extending from a rotating knob provides a surface for applying a lateral force for increasing rotational resistance on the first steering actuator.

10. The hand-operated catheter assembly of claim 1 wherein the first steering actuator comprises a knob that is mounted within the handle and wherein the exposed first control surface comprises a circumferential edge of the knob.

11. The hand-operated catheter assembly of claim 1 wherein the second steering actuator applies a tension to the steering line to affect flexing of a distal segment of the shaft.

12. The hand-operated catheter assembly of claim 11 wherein the second steering actuator comprises a steering pulley assembly through which the steering line passes.

13. The hand-operated catheter assembly of claim 11 wherein the second steering actuator comprises a steering pulley having a cleat upon which the steering line is wound.

14. The hand-operated catheter of claim 11, wherein the steering line resides in a lumen provided with a lumen liner comprising a high lubricity material that differs from the material of the shaft.

15. The hand-operated catheter assembly of claim 1 wherein the first steering actuator operates bi-directionally.

16. A hand-operated ultrasound catheter assembly comprising:
   an elongate flexible shaft having a proximal end and a distal end;
   an ultrasonic transducer mounted proximate the distal end;
   a set of steering lines running along the elongate flexible shaft; and
   a handle coupled to the shaft near the proximal end and adapted to steer, during an ultrasound imaging procedure, the ultrasonic transducer by applying a force to actuate one or more of the set of steering lines while simultaneously held within and manipulated by a single hand of an operator, the handle including:
      a housing having an elongate shape extending along a longitudinal axis and adapted for hand-held operation of the handle to affect steering of the ultrasonic transducer,
      a first steering actuator for controlling, via force applied to a first steering line of the set of steering lines, a position of the ultrasonic transducer, wherein the first steering actuator affects repositioning the ultrasonic transducer by repositioning a first control surface, exposed outside the housing of the handle, of the first steering actuator lengthwise in a direction parallel to the longitudinal axis of the housing of the handle by rotating the first steering actuator about a first shaft extending perpendicular to the longitudinal axis;
      a second steering actuator for controlling, via force applied to a second steering line of the set of steering lines, the position of the ultrasonic transducer, wherein the second steering actuator affects repositioning the ultrasonic transducer by repositioning a second control surface, exposed outside the housing of the handle, of the second steering actuator lengthwise in the direction parallel to the longitudinal axis of the housing of the handle by rotating the second steering actuator about a second shaft extending perpendicular to the longitudinal axis; and
      an actuator locking mechanism for holding at least the first steering actuator at a current position, wherein the actuator locking mechanism comprises a locking lever extending in a direction parallel to the longitudinal axis of the housing and comprising a set of teeth for engaging a complimentary inter-locking surface on the first steering actuator;
      wherein the exposed control surfaces of the first steering actuator and the second steering actuator are staggered along a shared surface of the housing of the handle such that a longer edge of the first exposed control surface and a longer edge of the second exposed control surface extend parallel to the longitudinal axis, but are offset with respect to one another.

17. The hand-operated catheter assembly of claim 1, wherein the first steering actuator includes a third control surface exposed outside of the housing of the handle opposite the first control surface.

18. The hand-operated catheter assembly of claim 17, wherein the second steering actuator includes a fourth control surface exposed outside of the housing of the handle opposite the second control surface.

19. The hand-operated catheter assembly of claim 18, wherein the exposed third control surface of the first steering actuator and the fourth control surface of the second steering actuator are staggered along the surface of the housing of the handle such that a longer edge of the third exposed control surface and a longer edge of the fourth exposed control surface extend parallel to the longitudinal axis, but are offset with respect to one another.

20. A hand-operated ultrasound catheter assembly comprising:
   an elongate flexible shaft having a proximal end and a distal end;
   an ultrasonic transducer mounted proximate the distal end; and
   a handle coupled to the shaft near the proximal end, the handle configured for single-handed control of a position of the ultrasonic transducer, the handle including:
      a housing having an elongate shape adapted for single-handed operation, the housing extending along a lengthwise axis;
      a first steering actuator for controlling a rotational position of a rotatable tip upon which the ultrasonic transducer is mounted, wherein the first steering actuator comprises a rotatable knob that rotates on axis transverse to the lengthwise axis of the housing, wherein the first steering actuator is positioned within the housing such that control surfaces of the first steering actuator are exposed through openings on opposing sides of the housing, wherein the first steering actuator affects repositioning of the rotatable tip upon which the ultrasonic transducer is mounted by repositioning the exposed control surfaces of the first steering actuator lengthwise along the housing of the handle,
      a second steering actuator for controlling the position of the ultrasonic transducer by controlling a flex of a distal segment of the shaft, wherein the second steering actuator comprises a rotatable knob that rotates on axis transverse to the lengthwise axis of the housing, wherein the first steering actuator is positioned within the housing and offset from the first steering actuator along the length and width of the housing such that control surfaces of the second steering actuator are exposed through openings on opposing sides of the housing in a staggered alignment relative to the exposed control surfaces of the first steering actuator and longer edges of the control surfaces of the first steering actuator extend along a first axis parallel to the lengthwise axis of the housing and longer edges of the control surfaces of the second steering actuator extend along a second axis parallel to but different than the first axis, wherein the second steering actuator controls the flex of the distal segment of the shaft by repositioning the exposed control surfaces of the second steering actuator lengthwise along the housing; and
      an actuator locking mechanism for holding at least the first steering actuator at a current position, wherein the actuator locking mechanism comprises a locking lever extending in a direction parallel to the longitudinal axis of the housing and comprising a set of teeth for engaging a complimentary inter-locking surface on the first steering actuator.

21. The hand-operated catheter assembly of claim 20 further comprising a torque member coupled to the rotatable tip and controlled by the first steering actuator to affect rotation of the rotatable tip.

22. The hand-operated catheter assembly of claim 21 wherein the torque member comprises a hollow inside through which a signal cable bundle passes.

23. The hand-operated catheter assembly of claim 20 wherein a screw knob disposed outside the housing is provided to adjust a varying degree of resistance.

24. The hand-operated catheter assembly of claim 20 wherein the second steering actuator applies a tension to a steering line to affect flexing of a distal segment of the shaft.

25. The hand-operated catheter of claim 24, wherein the steering line resides in a lumen provided with a lumen liner comprising a high lubricity material that differs from the material of the shaft.

\* \* \* \* \*